United States Patent [19]

Blaudin De The et al.

[11] Patent Number: 5,317,090

[45] Date of Patent: May 31, 1994

[54] STEROID/THYROID HORMONE RECEPTOR-RELATED GENE, WHICH IS INAPPROPRIATELY EXPRESSED IN HUMAN HEPATOCELLULAR CARCINOMA, AND WHICH IS A RETINOIC ACID RECEPTOR

[75] Inventors: Hughes Blaudin De The; Agnes Marchio; Pierre Tiollais; Anne Dejean, all of Paris; Nigel Brand, Strasbourg; Martin Petkovich, Strasbourg; Andree Krust, Strasbourg; Pierre Chambon, Strasbourg, all of France

[73] Assignee: Institut Pasteur, Paris, France

[21] Appl. No.: 989,902

[22] Filed: Dec. 11, 1992

Related U.S. Application Data

[63] Continuation of Ser. No. 860,577, Mar. 30, 1992, abandoned, which is a continuation of Ser. No. 751,612, Aug. 21, 1991, abandoned, which is a continuation of Ser. No. 330,405, Mar. 30, 1989, abandoned, which is a continuation-in-part of Ser. No. 278,136, Nov. 30, 1988, abandoned, which is a continuation-in-part of Ser. No. 209,009, Jun. 20, 1988, Pat. No. 5,149,781, which is a continuation-in-part of Ser. No. 134,130, Dec. 17, 1987, and Ser. No. 133,687, Dec. 16, 1987, abandoned.

[51] Int. Cl.$^5$ .............................. A61K 35/14
[52] U.S. Cl. .............................. 530/387.1; 530/387.9; 530/388.1; 530/388.22; 530/391.1
[58] Field of Search ............... 530/387.1, 387.9, 388.1, 530/388.2, 388.22, 391.1, 864; 435/7.1, 7.92, 70.2, 70.21, 172.2; 436/501, 547, 548

[56] References Cited

U.S. PATENT DOCUMENTS 4,859,609 8/1989 Dull et al. ..................... 435/501
4,981,784 1/1991 Evans et al. .

FOREIGN PATENT DOCUMENTS 8803168 5/1988 PCT Int'l Appl. .

OTHER PUBLICATIONS

Weinberger et al, *Nature*, vol. 318, pp. 670–672, 1985.
DeJean et al, *Nature*, vol. 322, pp. 70–72, 3 Jul. 1986.
"Hepatitis B Virus DNA Integration in a Sequence Homologous to V-erb-A and Steroid Receptor Genes in a Hepatocellular Carcinoma".
Greene et al, *Nature*, vol. 320 pp. pp. 134–139, 1986.
Green and Chambon, Nature, vol. 325, pp. 75–78, Jan. 1987.
Kumar et al., Cell, vol. 51, pp. 941–951, Dec. 1987.
Hollenberg et al., Cell, vol. 49, pp. 39–46, Apr. 1987.
Miesfeld et al., Science, vol. 230, pp. 423–437, Apr. 1987.
Klein-Hitpass et al., Cell, vol. 46, pp. 1053–10661, Sep. 1986.
Cato et al., The EMBO Journal, vol. 5, No. 9, pp. 2237–2240, 1986.
Krust et al., The EMBO Journal, vol. 5, No. 5, pp. 891–987, 1986.
Maniatis, Molecular Cloning-A Laboratory Manual, pp. 199–209, Cold Spring Harbor Laboratory, 1982.

*Primary Examiner*—Robert J. Hill, Jr.
*Assistant Examiner*—Laurie Scheiner
*Attorney, Agent, or Firm*—Finnegan, Henderson, Farabow, Garrett & Dunner

[57] ABSTRACT

A previously isolated hepatitis B virus (HBV) integration in a 147 bp cellular DNA fragment linked to hepatocellular carcinoma (HCC) was used as a probe to clone the corresponding complementary DNA from a human liver cDNA library. Nucleotide sequence analysis revealed that the overall structure of the cellular gene, which has been named hap, is similar to that of the DNA-binding hormone receptors. Six out of seven hepatoma and hepatoma-derived cell-lines express a 2.5 kb hap mRNA species which is undetectable in normal adult and fetal livers, but present in all non-hepatic tissues analyzed. Low stringency hybridization experiments revealed the existence of hap related genes in the human genome. The cloned DNA sequence is useful in the preparation of pure hap protein and as a probe in the detection and isolation of complementary DNA and RNA sequences. The hap protein is a retinoic acid (RA) receptor identified as RAR-$\beta$. The RAR-$\beta$ gene is transcriptionally up-regulated by retinoic acid (RA) and its promoter region may contain a RARE (retinoic acid responsive element).

11 Claims, 14 Drawing Sheets

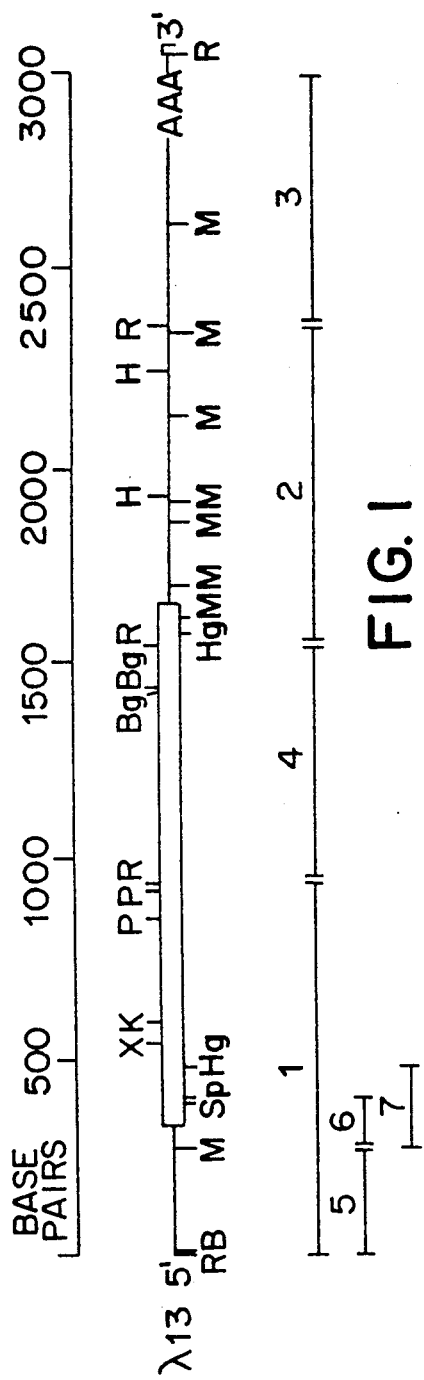

```
CGGGGTAGGATCCGGAACGCATTCGGAAGGCTTTTTGCAAGCATTTACTTGGAAGGAGAACTTGGGATCTTTCTG    75

GGAACCCCCCGCCCCGGCTGGATTGGCCGAGCAAGCCTGGAAAATGGTAAATGATCATTTCCATCAATTACAGGC   150

TTTTAGCTGGCTTGTCTGTCATAATTCATGATTCGGGGCTGGGAAAAAGACCAACAGCCTACGTGCCAAAAAAGG   225

GGCAGAGTTTGATGGAGTTGGGTGGACTTTTCTATGCCATTTGCCTCCACACCTAGAGGATAAGCACTTTTGCAC   300
                                   1                  10
                                   MetPheAspCysMetAspValLeuSerValSerProGlyGlnIleLeuAspPhe
ACATTCAGTGCAAGGGAGATCATGTTTGACTGTATGGATGTTCTGTCAGTGAGTCCTGGGCAAATCCTGGATTTC   375
             20                                   30                       40
TyrThrAlaSerProSerSerCysMetLeuGlnGluLysAlaLeuLysAlaCysPheSerGlyLeuThrGlnThr
TACACTGCGAGTCCGTCTTCCTGCATGCTCCAGGAGAAAGCTCTCAAAGCATGCTTCAGTGGATTGACCCAAACC   450
                       50                                  60
GluTrpGlnHisArgHisThrAlaGlnSerIleGluThrGlnSerThrSerSerGluGluLeuValProSerPro
GAATGGCAGCATCGGCACACTGCTCAATCAATTGAAACACAGAGCACCAGCTCTGAGGAACTCGTCCCAAGCCCC   525
            70                              80                       90
ProSerProLeuProProProArgValTyrLysProCysPheValCysGlnAspLysSerSerGlyTyrHisTyr
CCATCTCCACTTCCTCCCCCTCGAGTGTACAAACCCTGCTTCGTCTGCCAGGACAAATCATCAGGGTACCACTAT   600
                        100                                 110
GlyValSerAlaCysGluGlyCysLysGlyPhePheArgArgSerIleGlnLysAsnMetIleTyrThrCysHis
GGGGTCAGCGCCTGTGAGGGATGTAAGGGCTTTTTCCGCAGAAGTATTCAGAAGAATATGATTTACACTTGTCAC   675
                    120                             130                     140
ArgAspLysAsnCysValIleAsnLysValThrArgAsnArgCysGlnTyrCysArgLeuGlnLysCysPheGlu
CCAGATAAGAACTGTGTTATTAATAAAGTCACCAGGAATCGATGCCAATACTGTCGACTCCAGAAGTGCTTTGAA   750
                    150                             160
ValGlyMetSerLysGluSerValArgAsnAspArgAsnLysLysLysLysGluThrSerLysGlnGluCysThr
GTGGGAATGTCCAAAGAATCTGTCAGGAATGACAGGAACAAGAAAAAGAAGGAGACTTCGAAGCAAGAATGCACA   825
            170                             180                       190
GluSerTyrGluMetThrAlaGluLeuAspAspLeuThrGluLysIleArgLysAlaHisGlnGluThrPhePro
GAGAGCTATGAAATGACAGCTGAGTTGGACGATCTCACAGAGAAGATCCGAAAAGCTCACCAGGAAACTTTCCCT   900
                200                         210
SerLeuCysGlnLeuGlyLysTyrThrThrAsnSerSerAlaAspHisArgValArgLeuAspLeuGlyLeuTrp
TCACTCTGCCAGCTGGCTAAATACACCACGAATTCCAGTGCTGACCATCGAGTCCGACTGGACCTGGGCCTCTGG   975
                220                         230                        240
AspLysPheSerGluLeuAlaThrLysCysIleIleLysIleValGluPheAlaLysArgLeuProGlyPheThr
GACAAATTCAGTGAACTGGCCACCAAGTGCATTATTAAGATCGTGGAGTTTGCTAAACGTCTGCCTGGTTTCACT  1050
            250                                 260
GlyLeuThrIleAlaAspGlnIleThrLeuLeuLysAlaAlaCysLeuAspIleLeuIleLeuArgIleCysThr
GGCTTGACCATCGCAGACCAAATTACCCTGCTGAAGGCCGCCTGCCTGGACATCCTGATTCTTAGAATTTGCACC  1125
        270                             280                      290
ArgTyrThrProGluGlnAspThrMetThrPheSerAspGlyLeuThrLeuAsnArgThrGlnMetHisAsnAla
AGGTATACCCCAGAACAAGACACCATGACTTTCTCAGACGGCCTTACCCTAAATCGAACTCAGATGCACAATGCT  1200
                        300                                 310
GlyPheGlyProLeuThrAspLeuValPheThrPheAlaAsnGlnLeuLeuProLeuGluMetAspAspThrGlu
GGATTTGGTCCTCTGACTGACCTTGTGTTCACCTTTGCCAACCAGCTCCTGCCTTTGGAAATGGATGACACAGAA  1275
            320                             330                        340
ThrGlyLeuLeuSerAlaIleCysLeuIleCysGlyAspArgGlnAspLeuGluGluProThrLysValAspLys
ACAGGCCTTCTCAGTGCCATCTGCTTAATCTGTGGAGACCGCCAGGACCTTGAGGAACCGACAAAAGTAGATAAG  1350
                            350                             360
LeuGlnGluProLeuLeuGluAlaLeuLysIleTyrIleArgLysArgArgProSerLysProHisMetPhePro
CTACAAGAACCATTGCTGGAAGGACTAAAAATTTATATCAGAAAAAGACGACCCAGCAAGCCTCACATGTTTCCA  1425
        370                             380                      390
LysIleLeuMetLysIleThrAspLeuArgSerIleSerAlaLysGlyAlaGluArgValIleThrLeuLysMet
AAGATCTTAATGAAAATCACAGATCTCCGTAGCATCAGTGCTAAAGGTGCAGAGCGTGTAATTACCTTGAAAATG  1500
```

FIG. 2A

```
                    400                                      410
GluIleProGlySerMetProProLeuIleGlnGluMetMetGluAsnSerGluGlyHisGluProLeuThrPro
GAAATTCCTGGATCAATGCCACCTCTCATTCAAGAAATGATGGAGAATTCTGAAGGACATGAACCCTTGACCCCA 1575
       420                            430                            440
SerSerSerGlyAsnThrAlaGluHisSerProSerIleSerProSerSerValGluAsnSerGlyValSerGln
AGTTCAAGTGGGAACACAGCAGAGCACAGTCCTAGCATCTCACCCAGCTCAGTGGAAAACAGTGGGGTCAGTCAG 1650

SerProLeuValGlnSTOP
TCACCACTCGTGCAATAAGACATTTTCTAGCTACTTCAAACATTCCCCAGTACCTTCAGTTCCAGGATTTAAAAT 1725
GCAAGAAAAAACATTTTTACTGCTGCTTAGTTTTTGGACTGAAAAGATATTAAAACTCAAGAAGGACCAAGAAGT 1800
TTTCATATCTATCAATATATATACTCCTCACTGTGTAACTTACCTAGAAATACAAACTTTTCCAATTTTAAAAAA 1875
TCAGCCATTTCATGCAACCAGAAACTAGTTAAAAGCTTCTATTTTCCTCTTTGAACACTCAAGATGCATGGCAAA 1950
GACCCAGTCAAAATGATTTACCCCTGGTTAAGTTTCTGAAGACTTTGTACATACAGAAGTATGGCTCTGTTCTTT 2025
CTATACTGTATGTTTGGTGCTTTCCTTTTGTCTTGCATACTCAAAATAACCATGACACCAAGGTTATGAAATAGA 2100
CTACTGTACACGTCTACCTAGGTTCAAAAAGATAACTGTCTTGCTTTCATGGAATAGTCAAGACATCAAGGTAAG 2175
GAAACAGGACTATTGACAGGACTATTGTACAGTATGACAAGATAAGGCTGAAGATATTCTACTTTAGTTAGTATG 2250
GAAGCTTGTCTTTGCTCTTTCTGATGCTCTCAAACTGCATCTTTTATTTCATGTTGCCCAGTAAAAGTATACAAA 2325
TTCCCTGCACTAGCAGAAGAGAATTCTGTATCAGTGTAACTGCCAGTTCAGTTAATCAAATGTCATTTGTTCAAT 2400
TGTTAATGTCACTTTAAATTAAAAGTGGTTTATTACTTGTTTAATGACATAACTACACAGTTAGTTAAAAAAAAT 2475
TTTTTTACAGTAATGATAGCCTCCAAGGCAGAAACACTTTTCAGTGTTAAGTTTTTGTTTACTTGTTCACAAGCC 2550
ATTAGGGAAATTTCATGGGATAATTAGCAGGCTGGTCTACCACTGGACCATGTAACTCTAGTGTCCTTCCTGATT 2625
CATGCCTGATATTGGGATTTTTTTCCAGCCCTTCTTGATGCCAAGGGCTAATTATATTACATCCCAAAGAAACAG 2700
GCATAGAATCTGCCTCCTTTGACCTTGTTCAATCACTATGAAGCAGAGTGAAAGCTGTGGTAGAGTGGTTAACAG 2775
ATACAACTGTCAGTTTCTTAGTTCTCATTTAAGCACTAGTGGAATTTTTTTTTTGATATATTAGCAAGTCTGTG 2850
ATGTACTTTCACTGGCTCTGTTTGTACATTGAGATTGTTTGTTAACAATGCTTTCTATGTTCATATACTGTTTA 2925
CCTTTTTCCATGGAGTCTCCTGGCAAAGAATAAAATATATTTATTTTAAAAAAAAAAAAAAAAAAAAAA 2992
```

FIG. 2B

CONTROL

CONTROL

FIG. 6

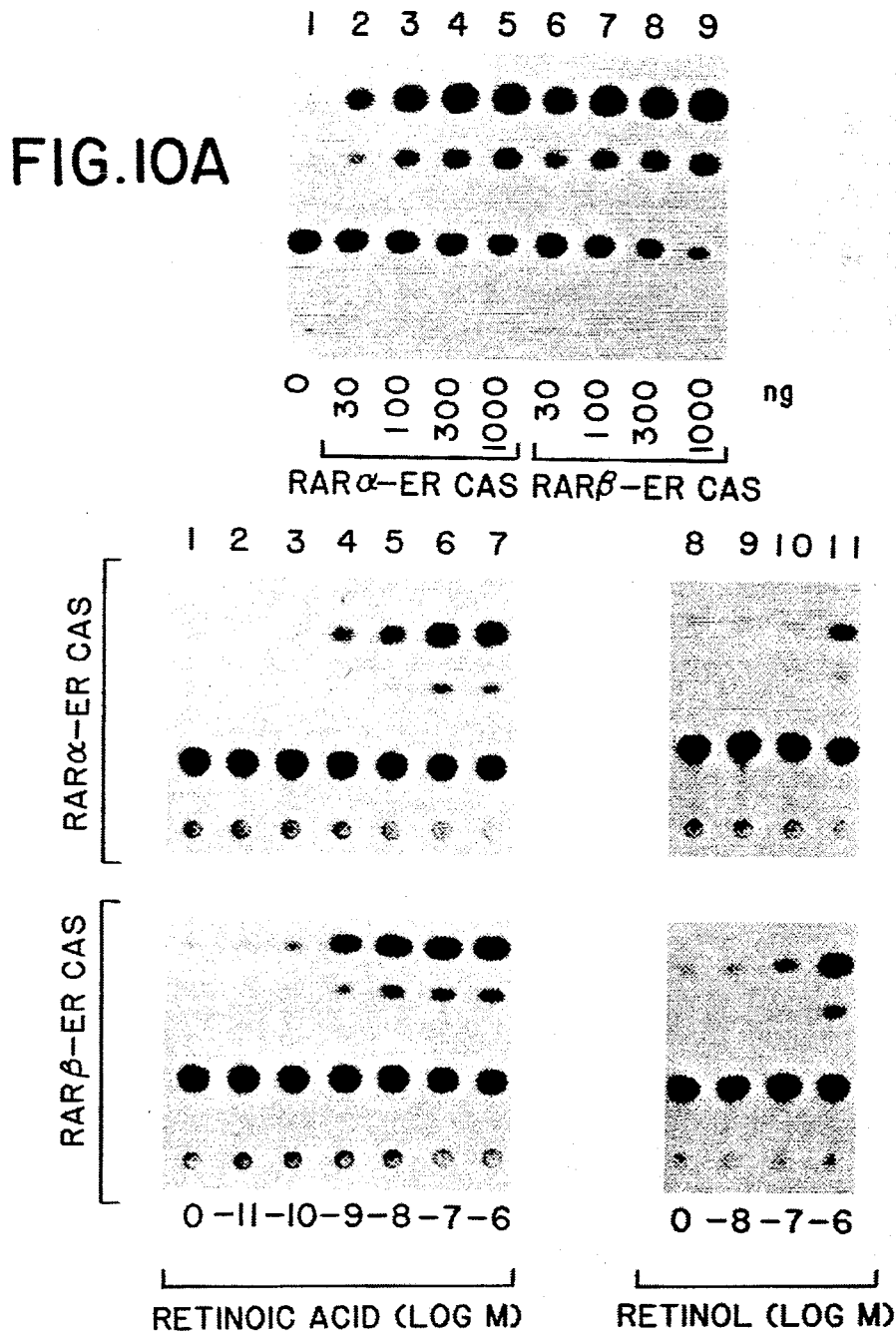

STEROID/THYROID HORMONE RECEPTOR-RELATED GENE, WHICH IS INAPPROPRIATELY EXPRESSED IN HUMAN HEPATOCELLULAR CARCINOMA, AND WHICH IS A RETINOIC ACID RECEPTOR

This application is a continuation of application Ser. No. 07/860,577, now abandoned, filed Mar. 30, 1992, which is a continuation of application Ser. No. 07/751,612, now abandoned, filed Aug. 21, 1991, which is a continuation of application Ser. No. 07/330,405, now abandoned, filed Mar. 30, 1989, which is a continuation-in-part of application Ser. No. 07/278,136, now abandoned, filed Nov. 30, 1988, which is a continuation-in-part of application Ser. No. 07/209,009, now U.S. Pat. No. 5,149,781, filed Jun. 20, 1988, which is a continuation-in-part of application Ser. No. 07/134,130, filed Dec. 17, 1987, and a continuation-in-part of application Ser. No. 07/133,687, now abandoned, filed Dec. 16, 1987. The entire disclosure of each of these applications is relied upon and incorporated herein by reference.

BACKGROUND OF THE INVENTION

This invention relates to nucleotide sequences, polypeptides encoded by the nucleotide sequences, and to their use in diagnostic and pharmaceutical applications.

Primary hepatocellular carcinoma (HCC) represents the most common cancer, especially in young men, in many parts of the world (as in China and in much of Asia and Africa) (reviewed in Tiollais et al., 1985). Its etiology was investigated mostly by epidemiological studies, which revealed that, beyond some minor potential agents such as aflatoxin and sex steroid hormones, hepatitis B virus (HBV) chronic infection could account for a large fraction of liver cancers (Beasley and Hwang, 1984).

HBV DNA has been found to be integrated in the genome of most cases of HCCs studied (Edman et al., 1980; Brechot et al., 1980; Chakraborty et al., 1980; Chen et al., 1982). Nonetheless the role of those sequences in liver oncogenesis remains unclear.

A single HBV integration in a short liver cell sequence from a human HCC sample has been reported recently. The sequence was found to be homologous to steroid receptor genes and to the cellular proto-oncogene c-erbA (Dejean et al., 1986).

Ligand-dependent transcriptional activators, such as steroid or thyroid hormone receptors, have recently been cloned allowing rapid progress in the understanding of their mechanism of action. Nevertheless, there exists a need in the art for the identification of transcripts that may encode for activational elements, such as nuclear receptors, that may play a role in hepatocarcinogenesis. Such findings would aid in identifying corresponding transcripts in susceptible individuals. In addition, identification of transcripts could aid in elucidating the mechanisms by which HCC occurs.

Retinoids, a class of compounds including retinol (vitamin A), retinoic acid (RA), and a series of natural and synthetic derivatives, exhibit striking effects on cell proliferation, differentiation, and pattern formation during development (Strickland and Mahdavi, 1978; Breitman et al., 1980; Roberts and Sporn, 1984; Thaller and Eichele, 1987). Until recently, the molecular mechanism by which these compounds exert such potent effects was unknown, although retinoids were thought to modify their target cells through a specific receptor.

Except for the role of retinoids in vision, their mechanism of action is not well understood at the molecular level. Several possible mechanisms have been suggested. One hypothesis proposes that retinoids are needed to serve as the lipid portion of glycolipid intermediates involved in certain specific glycosylation reactions. Another mechanism, which may account for the various effects of retinoids on target cells, is that they alter genomic expression in such cells. It has been suggested that retinoids may act in a manner analogous to that of the steroid hormones and that the intracellular binding proteins (cellular retinol-binding and retinoic acid-binding protein) play a critical part in facilitating the interaction of retinoids with binding sites in the cell nucleus.

For example, the observation that the RA-induced differentiation of murine F9 embryonal carcinoma cells is accompanied by the activation of specific genes has led to the proposal that RA, like the steroid and thyroid hormones, could exert its transcriptional control by binding to a nuclear receptor (Roberts and Sporn, 1984). However, the biochemical characterization of this receptor had been hampered by high affinity RA-binding sites corresponding to the cellular retinoic acid binding protein (CRABP), which is thought to be a cytoplasmic shuttle for RA (Chytil and Ong, 1984).

In any event, retinoids are currently of interest in dermatology. The search for new retinoids has identified a number of compounds with a greatly increased therapeutic index as compared with naturally occurring retinoids. Extensive clinical testing of two of these retinoids, 13-cis-retinoic acid and the aromatic analog etretinate, has lead to their clinical use in dermatology. In addition, several lines of evidence suggest that important relations exist between retinoids and cancer. A number of major diseases, in addition to cancer, are characterized by excessive proliferation of cells, often with excessive accumulation of extracellular matrix material. These diseases include rheumatoid arthritis, psoriasis, idiopathic pulmonary fibrosis, scleroderma, and cirrhosis of the liver, as well as the disease process atherosclerosis. The possibility exists that retinoids, which can influence cell differentiation and proliferation, may be of therapeutic value in some of these proliferative diseases. There exists a need in the art for reagents and methods for carrying out studies of receptor expression and effector function to determine whether candidate drugs are agonists or antagonists of retinoid activity in biological systems.

There also exists a need in the art for identification of retinoic acid receptors and for sources of retinoic acid receptors in highly purified form. The availability of the purified receptor would make it possible to assay fluids for agonists and antagonists of the receptor.

SUMMARY OF THE INVENTION

This invention aids in fulfilling these needs in the art. More particularly, this invention provides a cloned DNA sequence encoding for a polypeptide of a newly identified cellular gene, which has been named hap. The DNA sequence has the formula shown in FIG. 2. More particularly, the sequence comprises the coding region as follows:

ATGTTTGACTGTATGGATGTTCTGTCAGTGAGTCCTGGGCAAATCCTGATTCTACACTGCGAGTCC

GTCTTCCTGCATGCTCCAGGAGAAAGCTCTCAAAGCATGCTTCAGTGGATTGACCCAAACCGAATG

GCAGCATCGGCACACTGCTCAATCAATTGAAACACAGAGCACCAGCTCTGAGGAACTCGTCCCAAG

CCCCCCATCTCCACTTCCTCCCCCTCGAGTGATCAAACCCTGCTTCGTCTGCCAGGACAAATCATC

AGGGTACCACTATGGGGTCAGCGCCTGTGAGGGATGAAGGGCTTTTTCCGCAGAAGTATTCAGAAG

AATATGATTTACACTTGTCACCGAGATAAGAACTGTGTTATTAATAAAGTCACCAGGAATCGATGC

CAATACTGTCGACTCCAGAAGTGCTTTGAAGTGGGAATGTCCAAAGAATCTGTCAGGAATGACAGG

AACAAGAAAAGAAGGAGACTTCGAAGCAAGAATGCACAGAGAGCTATGAAATGACAGCTGAGTTG

GACGATCTCACAGAGAAGATCCGAAAAGCTCACCAGGAAACTTTCCCTTCACTCTCGCAGCTGGGT

AAATACACCACGAATTCCAGTGCTGACCATCGAGTCCGACTGGACCTGGGCCTCTGGGACAAATTC

AGTGAACTGGCCACCAAGTGCATTATTAAGATCGTGGAGTTTGCTAAACGTCTGCCTGGTTTCACT

GGCTTGACCATCGCAGACCAAATTACCCTGCTGAAGGCCGCCTGCCTGGACATCCTGATTCTTAGA

ATTTGCACCAGGTATACCCCAGAACAAGACACCATGACTTTCTCAGACGGCCTTACCCTAAATCGA

ACTCAGATGCACAATGCTGGATTTGGTCCTCTGACTGACCTTGTGTTCACCTTTGCCAACCAGCTC

CTGCCTTTGGAAATGGATGACACAGAAACAGGCCTTCTCAGTGCCATCTGCTTAATCTGTGGAGAC

CGCCAGGACCTTGAGGAACCGACAAAAGTAGATAAGCTACAAGAACCATTGCTGGAAGCACTAAAA

ATTTATATCAGAAAAAGACGACCCAGCAAGCCTCACATGTTTCCAAAGATCTTAATGAAAATCACA

GATCTCCGTAGCATCAGTGCTAAAGGTGCAGAGCGTGTAATTACCTTGAAAATGGAAATTCCTGGA

TCAATGCCACCTCTCATTCAAGAAATGATGGAGAATTCTGAAGGACATGAACCCTTGACCCCAAGT

TCAAGTGGGAACACAGCAGAGCACAGTCCTAGCATCTCACCCAGCTCAGTGGAAAACAGTGGGGTC

AGTCAGTCACCACTCGTGCAATAA.

The vector containing the coding region is pCOD20 in a pTZ18 vector (derived from pBR322). This pCOD20 vector is accessible at Collection Nationale de Cultures de Micro-organismes (C.N.C.M.) of Institut Pasteur, 28 rue du Docteur Roux, 75724 Paris Cedex 15, France, under accession No. I-852, as of Mar. 30, 1989. The pTZ18 is available and sold by Pharmacia Molecular Biologicals Company (Sweden). The invention also covers variants and fragments of the DNA sequence. The DNA sequence is in a purified form.

This invention also provides a probe consisting of a radionuclide bonded to the DNA sequence of the invention.

In addition, this invention provides a hybrid duplex molecule consisting essentially of the DNA sequence of the invention hydrogen bonded to a nucleotide sequence of complementary base sequence, such as DNA or RNA.

Further, this invention provides a polypeptide comprising an amino acid sequence of hap protein, wherein the polypepetide contains the amino acid sequence shown in FIG. 2. More particularly, the amino acid sequence comprises:

MetPheAspCysMetAspValLeuSerValSerProGlyGlnIle LeuAspPheTyrThrAla

SerProSerSerCysMetLeuGlnGluLysAlaLeuLysAlaCys PheSerGlyLeuThrGln

ThrGluTrpGlnHisArgHisThrAlaGlnSerIleGluThrGln SerThrSerSerGluGlu

LeuValProSerProProSerProLeuProProProArgValTyr

-continued

LysProCysPheValCys

GlnAspLysSerSerGlyTyrHisTyrGlyValSerAlaCysGlu GlyCysLysGlyPhePhe

ArgArgSerIleGlnLysAsnMetIleTyrThrCysHisArgAsp LysAsnCysValIleAsn

LysValThrArgAsnArgCysGlnTyrCysArgLeuGlnLysCys PheGluValGlyMetSer

LysGluSerValArgAsnAspArgAsnLysLysLysLysGluThr SerLysGlnGluCysThr

GluSerTyrGluMetThrAlaGluLeuAspAspLeuThrGluLys IleArgLysAlaHisGln

GluThrPheProSerLeuCysGlnLeuGlyLysTyrThrThrAsn SerSerAlaAspHisArg

ValArgLeuAspLeuGlyLeuTrpAspLysPheSerGluLeuAla ThrLysCysIleIleLys

IleValGluPheAlaLysArgLeuProGlyPheThrGlyLeuThr IleAlaAspGlnIleThr

LeuLeuLysAlaAlaCysLeuAspIleLeuIleLeuArgIleCys ThrArgTyrThrProGlu

GlnAspThrMetThrPheSerAspGlyLeuThrLeuAsnArgThr GlnMetHisAsnAlaGly

PheGlyProLeuThrAspLeuValPheThrPheAlaAsnGlnLeu LeuProLeuGluMetAsp

AspThrGluThrGlyLeuLeuSerAlaIleCysLeuIleCysGly AspArgGlnAspLeuGlu

GluProThrLysValAspLysLeuGlnGluProLeuLeuGluAla

-continued

LeuLysIleTyrIleArg

LysArgArgProSerLysProHisMetPheProLysIleLeuMet
LysIleThrAspLeuArg

SerIleSerAlaLysGlyAlaGluArgValIleThrLeuLysMet
GluIleProGlySerMet

ProProLeuIleGlnGluMetMetGluAsnSerGluGlyHisGlu
ProLeuThrProSerSer

SerGlyAsnThrAlaGluHisSerProSerIleSerProSerSer
ValGluAsnSerGlyVal

SerGlnSerProLeuValGln.

The invention also covers serotypic variants of the polypeptide and fragments of the polypeptide. The polypeptide is free from human serum proteins, virus, viral proteins, human tissue, and human tissue components. Preferably, the polypeptide is free from human, blood-derived protein.

The hap protein (hap for hepatoma) exhibits strong homology with the human retinoic acid receptor (RAR) de Thé, H., Marchio, A., Tiollais, P. & Dejean, A. *Nature* 330, 667–670 (1987), Petkovich, M., Brand, N. J., Krust, A. & Chambon, P. *Nature* 330, 444–450 (1987), a receptor has been recently characterized Petkovich, M., Brand, N. J., Krust, A. & Chambon, P. *Nature* 330, 444–450 (1987), Giguere, V., Ong, E. S., Segui, P. & Evans, R. M. *Nature* 330, 624–629 (1987). To test the possibility that the hap protein might also be a retinoid receptor, a chimaeric receptor was created by replacing the putative DNA binding domain of hap with that of the human oestrogen receptor (ER). The resulting hap-ER chimaera was then tested for its ability to trans-activate an oestrogen-responsive reporter gene (vit-tk-CAT) in the presence of possible receptor ligands. It was discovered that retinoic acid (RA) at physiological concentrations is effective in inducing the expression of this reporter gene by the hap-ER chimaeric receptor. See *Nature*, 332: 850–853 (1988). This demonstrates the existence of two human retinoic acid receptors designated RAR-α and RAR-β.

More particularly, it has been discovered that the hap protein is a second retinoic acid receptor. Thus, the expression "hap protein" is used interchangeably herein with the abbreviation "RAR-β" for the second human retinoic acid receptor.

Also, this invention provides a process for selecting a nucleotide sequence coding for hap protein or a portion thereof from a group of nucleotide sequences comprising the step of determining which of the nucleotide sequences hybridizes to a DNA sequence of the invention. The nucleotide sequence can be a DNA sequence or an RNA sequence. The process can include the step of detecting a label on the nucleotide sequence.

Still further, this invention provides a recombinant vector comprising lambda-NM1149 having an EcoRI restriction endonuclease site into which has been inserted the DNA sequence of FIG. 2. This clone is "λ13". It has been recloned in a pBR327 vector named phap, which is accessible in C.N.C.M. under accession No. I-853, deposited Mar. 30, 1989. The invention also provides plasmid pCOD20, which comprises the DNA sequence of the invention exclusively corresponding to the coding region.

This invention provides an *E. coli* bacterial culture in a purified form, wherein the culture comprises *E. coli* cells containing DNA, wherein a portion of the DNA comprises the DNA sequence of the invention. Preferably, the *E. coli* is stain TG-1.

In addition, this invention provides a method of using the purified retinoic acid receptor of the invention for assaying a medium, such as a fluid, for the presence of an agonist or antagonist of the receptor and to dose it (quantification in the sera of a patient, for example). In general, the method comprises providing a known concentration of a proteinaceous receptor of the invention, incubating the receptor with a ligand of the receptor and a suspected agonist or antagonist under conditions sufficient to form a ligand-receptor complex, and assaying for ligand-receptor complex or for free ligand or for non-complex receptor. The assay can be conveniently carried out using labelled reagents as more fully described hereinafter, and conventional techniques based on nucleic acid hybridization, immunochemistry, and chromotograph, such as TLC, HPLC, and affinity chromatography.

In another method of the invention, a medium is assayed for stimulation of transcription of the RAR-β gene or translation of the gene by an agonist or antagonist. For example, β-receptor binding retinoids can be screened in this manner.

BRIEF DESCRIPTION OF THE DRAWINGS

This invention will be described in greater detail with reference to the drawings in which FIG. 1 is a restriction map of human liver hap cDNA;

FIGS. 2A and 2B are the nucleotide sequence of human liver hap cDNA and a predicted amino acid sequence of human liver hap cDNA;

FIG. 6 shows the alignment of hap translated amino acid sequence with several known sequences for thyroid and steroid hormone receptors;

FIG. 7 is a schematic alignment of similar regions identified as A/B, C, D, and E of the amino acid sequences of FIG. 6;

FIG. 10(a) shows CAT activity resulting from activation of the reporter gene vit-tk-CAT by the chimaeric receptors RAR-α-ER.CAS and RAR-β-ER.CAS in the presence of retinoic acid;

FIG. 10(b) shows the effect of retinoic acid concentration on the induction of CAT activity by either RAR-α-ER.CAS or RAR-β-ER.CAS;

Figure 11:
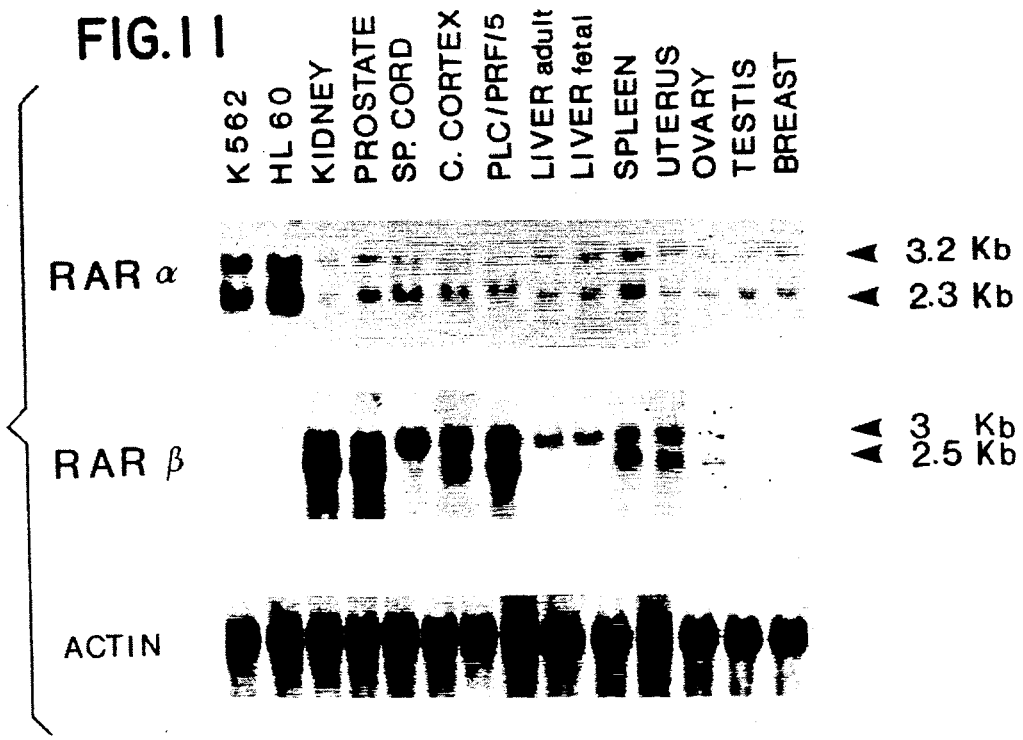
Figure 12A:
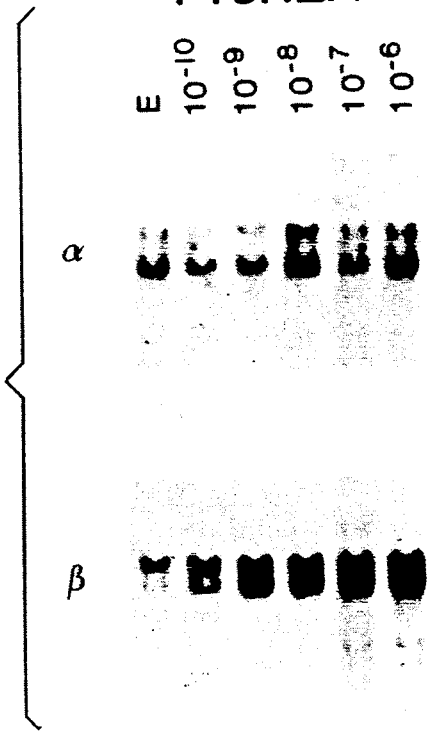
Figure 12B:
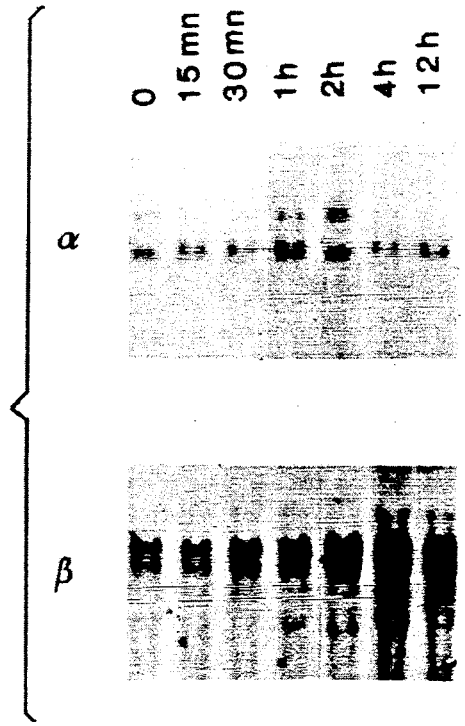
Figure 13:
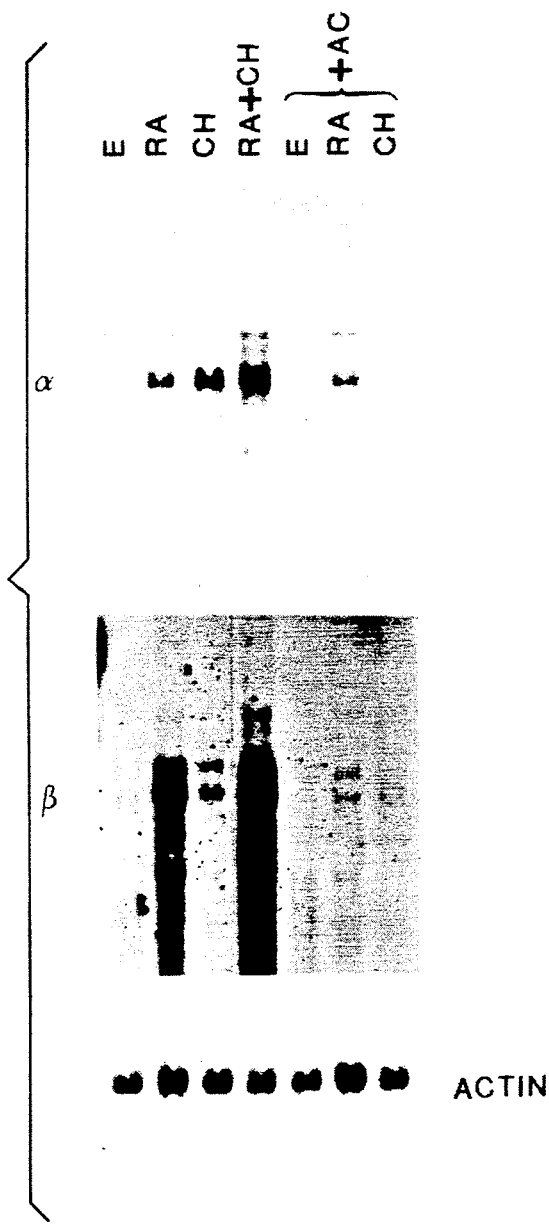
Figure 16:
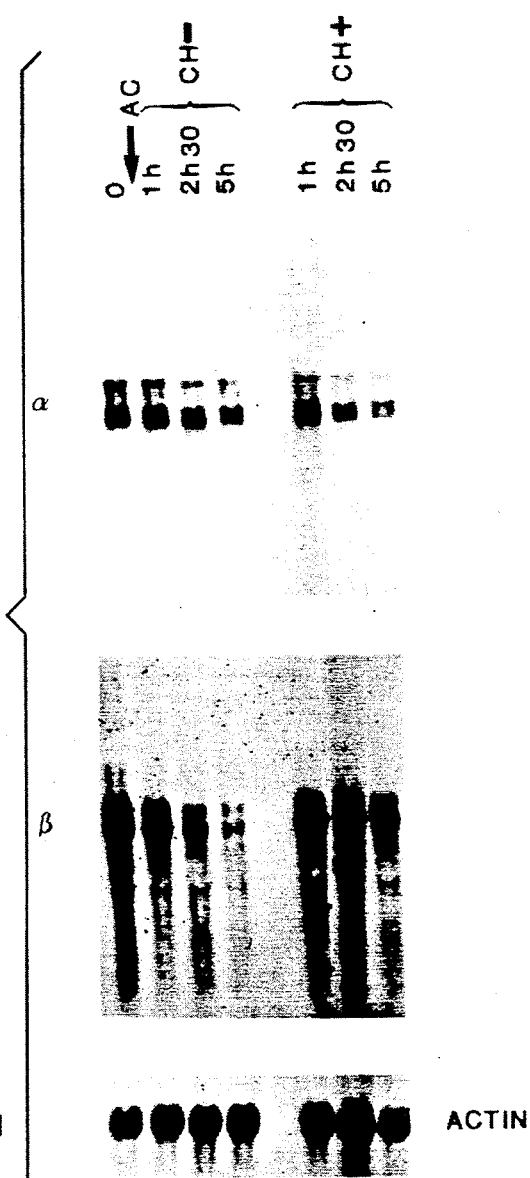
Figure 14:
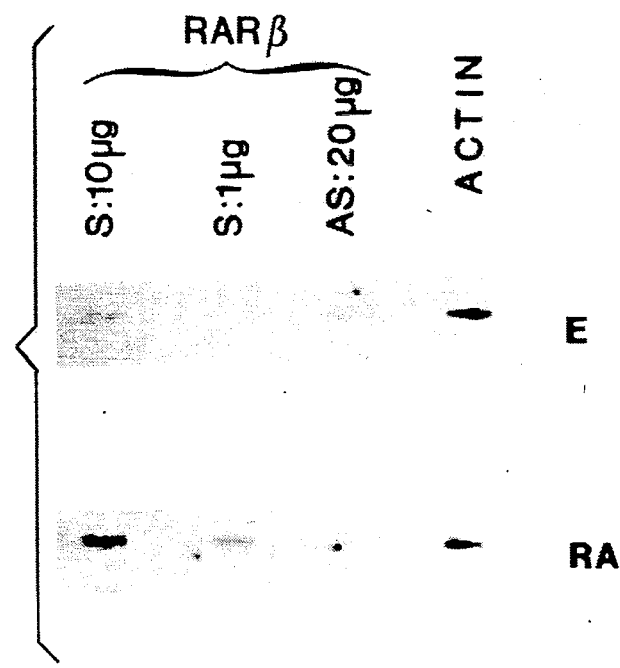
Figure 15:
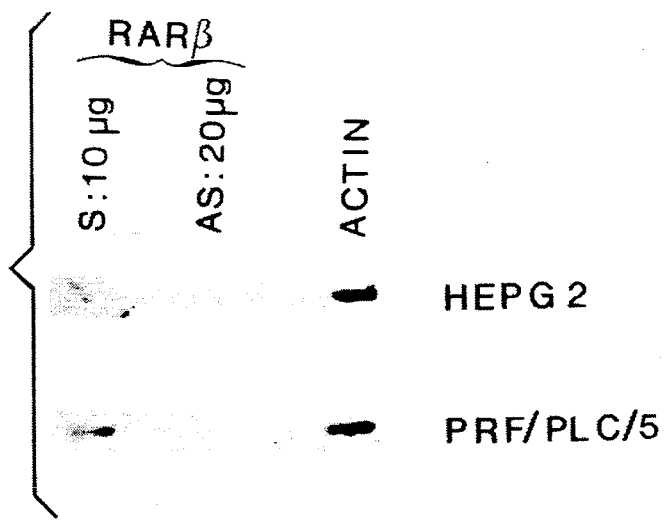
Figures 17, 18:
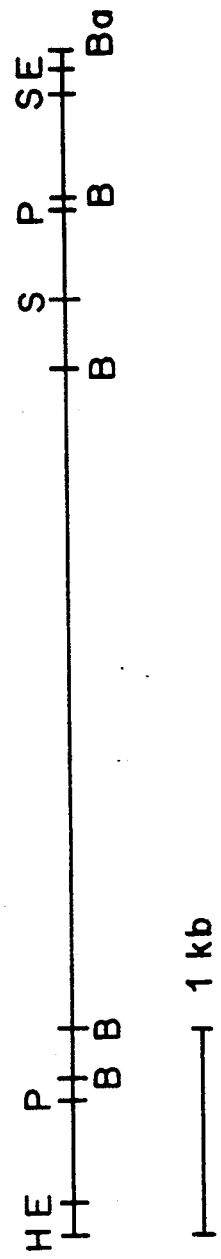

ER.CAS (solid circles) or RAR-α-ER.CAS (open circles), while the right panel; is a graph of the results shown in FIG. 10(b) in response to retinoic acid (solid line) or retinoid (broken line);

FIG. 11 shows the tissue distribution of RAR α and β transcripts;

FIGS. 12A and 12B show the dose- and time-response of RAR α and β transcripts after retinoic acid treatment of PLC/PRF/5 cells;

FIG. 13 shows the effect of RNA and protein synthesis inhibitors on the levels of RAR α and β mRNAs;

FIG. 14 reports the results of nuclear run-on analysis of RAR β gene transcription after RA treatment;

FIG. 15 reports the results of nuclear run-on analysis of RAR β transcription in two hepatoma cell-lines;

FIG. 16 shows the resulting kinetic analysis of RAR mRNA degradation;

FIG. 17 depicts a nucleotide sequence analysis extending a λ 13 RAR-β by 72 bp; and FIG. 18 is a complete restriction map of a cloned HindIII-BamHI genomic DNA insert containing the nucleotide sequence of FIG. 17. It contains the promoter region of the RARβ gene.

DETAILED DESCRIPTION OF PREFERRED EMBODIMENTS

A. Identification of a Protein, Named hap Protein, Having DNA-Binding and Ligand-Binding Domains, and Identification of the DNA Sequence Encoding hap Protein As previously noted, ligand-dependent transcriptional activators, such as steroid or thyroid hormone receptors, have recently been cloned. The primary structure and expression of a new gene, hap, closely related to steroid or thyroid hormone receptor genes have now been discovered. The hap product exhibits two regions highly homologous to the conserved DNA- and hormone-binding domains of previously cloned receptors.

More particularly, the cloning of a cDNA corresponding to a novel steroid/thyroid hormone receptor-related gene has been achieved. The cDNA was recovered from a human liver cDNA library using a labelled cellular DNA fragment previously isolated from a liver tumor. The fragment contained a 147 bp putative exon in which HBV inserted. The sequence of this cellular gene, which is referred to herein as hap for hepatoma, reveals various structural features characteristic of c-erbA/steroid receptors (Dejean et al., 1986). The receptor-related protein is likely to be a novel member of the superfamily of transcriptional regulatory proteins that includes the thyroid and steroid hormone receptors.

It has been discovered that the hap gene is transcribed at low level in most human tissues, but the gene is overexpressed in prostate and kidney. Moreover, six out of seven hepatoma and hepatoma-derived cell lines express a small hap transcript, which is undetectable in normal adult and fetal livers, but is present in all non-hepatic tissues tested. Altered expression of hap may be involved in liver oncogenesis.

These findings, as well as other discoveries relating to this invention, will now described in detail.

A.1 Cloning and Sequencing of a Hap cDNA

A human liver cDNA library was screened using a nick-translated 350 bp EcoRI genomic fragment (MNT probe) previously cloned from a hepatoma sample. The fragment contained the putative 147 bp cellular exon in which HBV integration took place (Dejean et al., 1986).

Four positive 3' co-terminal clones were isolated from the 2×10⁶ plaques screened and the restriction maps were deduced for each of the cDNA clone EcoRI inserts. The longest one was identified lambda-13. The restriction map of lambda-13 is shown in FIG. 1.

Referring to FIG. 1, the insert of clone lambda-13 is nearly a full-length cDNA for the hap gene. Noncoding sequences (lines) and coding sequences (boxed portion) are indicated. Restriction sites are:

R EcoRI
Bg BglII
M MaeI
X XhoI
K KpnI
P PvuII
B BamHI
H HindIII.

The lambda-13 clone was subjected to nucleotide sequence analysis. The nucleotide sequence is shown in FIG. 2. The nucleotide sequence of the hap cDNA is presented in the 5' to 3' orientation. The numbers on the right refer to the position of the nucleotides. Numbers above the deduced translated sequence indicate amino acid residues. The four short open reading frames in the 5' untranslated region are underlined. Adenosine residues (20) are found at the 3' end of lambda-13. The putative polyadenylation signal site (AATAAA) is boxed. The region homologous to the DNA-binding domain of known thyroid/steroid hormone receptors is indicated by horizontal arrows. The exon, previously cloned from a HCC sample genomic DNA library and in which HBV integration took place, is bracketed.

This invention of course includes variants of the nucleotide sequence shown in FIG. 2 encoding hap protein or a serotypic variant of hap protein exhibiting the same immunological reactivity as hap protein.

The DNA sequence of the invention is in a purified form. Generally, the DNA sequence is free of human serum proteins, viral proteins, and nucleotide sequences encoding these proteins. The DNA sequence of the invention can also be free of human tissue.

The DNA sequence of the invention can be used as a probe for the detection of a nucleotide sequence in a biological material, such as tissue or body fluids. The polynucleotide probe can be labeled with an atom or inorganic radical, most commonly using a radionuclide, but also perhaps with a heavy metal.

In some situations it is feasible to employ an antibody which will bind specifically to the probe hybridized to a single stranded DNA or RNA. In this instance, the antibody can be labeled to allow for detection. The same types of labels which are used for the probe can also be bound to the antibody in accordance with known techniques.

Conveniently, a radioactive label can be employed. Radioactive labels include $^{32}P$, $^{3}H$, $^{14}C$, or the like. Any radioactive label can be employed, which provides for an adequate signal and has sufficient half-life. Other labels include ligands, that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

Ligands and anti-ligands can be varied widely. Where a ligand has a natural receptor, namely ligands such as biotin, thyroxine, and cortisol, these ligands can be used in conjunction with labeled naturally occurring receptors. Alternatively, any compound can be used, either haptenic or antigenic, in combinations with an antibody.

Enzymes of interest as labels are hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin and luminol.

A.2. Amino Acid Sequence of Protein Encoded by hap Gene

Based upon the sequence of the hap cDNA, the amino acid sequence of the protein encoded by hap gene was determined. With reference to FIG. 2, the deduced amino acid sequence encoded by the gene reveals a long open reading frame of 448 amino acids corresponding to a predicted polypeptide of relative molecular mass 51,000.

A putative initiator methionine codon and an in-frame terminator codon are positioned respectively at nucleotides 322 and 1666 in the sequence (FIG. 2). However, two other methionine codons are found 4 and 26 triplets downstream from the first ATG making the determination of the initiation site equivocal.

The coding sequence is preceded by a 5' region of at least 321 nucleotides which contains four short open reading frames delineated by initiator and stop codons (FIG. 2). Translation usually starts, in eukaryotes, at the 5' most ATG triplet, but the finding of open reading frames in the 5' 'untranslated' region is not unprecedented (Kozak, 1986). It is not known yet whether those sequences are used for translation and exert any function in the cell.

In the 3' untranslated region, 1326 nucleotides long, no long open reading frame is present. A putative polyadenylation signal (AATAAA) is found 19 bp upstream from the polyadenylation site.

It will be understood that the present invention is intended to encompass the protein encoded by the hap gene, i.e. hap protein, and fragments thereof in highly purified form. The hap protein can be expressed in a suitable host containing the DNA sequence of the invention. This invention also includes polypeptides in which all or a portion of the binding site of hap protein is linked to a larger carrier molecule, such as a polypeptide or a protein, and in which the resulting product exhibits specific binding in vivo and in vitro. In this case, the polypeptide can be smaller or larger than the proteinaceous binding site of the protein of the invention.

It will be understood that the polypeptide of the invention encompasses molecules having equivalent peptide sequences. By this it is meant that peptide sequences need not be identical. Variations can be attributable to local mutations involving one or more amino acids not substantially affecting the binding capacity of the polypeptide. Variations can also be attributable to structural modifications that do not substantially affect binding capacity. Thus, for example, this invention is intended to cover serotypic variants of hap protein.

Three particular regions of hap gene are of interest. Two of them are located in the D region (amino acids comprised between 46 and 196), which have been shown by the inventors to be highly immunogenic. Amino acids 46-196 have the sequence:

GlnHisArgHisThrAlaGlnSerIleGluThrGlnSerThrSerSerGluGlu

LeuValProSerProProSerProLeuProProProArgValTyrLysProCysPheValCys

GlnAspLysSerSerGlyTyrHisTyrGlyValSerAlaCysGluGlyCysLysGlyPhePhe

ArgArgSerIleGlnLysAsnMetIleTyrThrCysHisArgAspLysAsnCysValIleAsn

LysValThrArgAsnArgCysGlnTyrCysArgLeuGlnLysCysPheGluValGlyMetSer

LysGluSerValArgAsnAspArgAsnLysLysLysLysGluThrSerLysGlnGluCysThr

GluSerTyrGluMetThrAlaGluLeuAspAspLeuThrGluLysIleArgLysAlaHisGln

GluThrPheProSerLeuCys.

One peptide of interest in the D region is comprised of acids 151-167 and has the sequence:

ValArgAsnAspAsgAsnLysLysLysLysGluThrSerLysGlnGluCys.

A second peptide in the D region is located between amino acids 175 and 185. This peptide has the amino acid sequence:

AlaGluLeuAspAspLeuThrGluLysIleArg.

Another peptide of interest is located at the end of C region between amino acids 440 and 448. This peptide has the amino acid sequence:

GlyValSerGlnSerProLeuValGln.

Other peptides having formulas derived from the nucleotide sequence of hap gene can be used as reagents, particularly to obtain antibodies for diagnostic purposes, as defined hereinabove.

The most favorable region is found in the hinge region (amino acids 147 to 193). This region includes amino acids 150 to 170, corresponding to the following criteria:

The region includes very hydrophilic sequences, namely, the sequences 154-160 (No. 1/Hopp); 155-161 (No. 1/Doolittle); 155-159 (No. 1/acrophilic).

The region includes a peptide, namely, amino acids 156-162, No. 5 in mobility.

The polypeptide of this region has a low probability of adopting a structure in the form of a folded sheet or a helix, but, in contrast, a good probability of an omega loop and one beta-turn, very marked in the Asp-Arg-Asn-Lys tetrapeptide.

The region does not have a potential site of N-glycosylation nearby; several suggestions in this zone can be made:

Val—Arg—Asn—Asp—Arg—Asn—Lys—Lys—Lys—Lys—Glu—Thr—Ser—Lys—

Gln—Glu—Cys. (peptide 1);

Peptide 1 corresponds to amino acids 151–167 and permits finding Cys 167, which is present in the sequence and enables attachment to a carrier (it will be noted that this peptide corresponds to a consensus sequence of phosphorylation by kinase A).

Peptide 1 can be shortened by N-turn while preserving the beta-turn and by C-turn while replacing Ser by Cys to maintain the possibility of coupling at this level:

(peptide 2)

Asn—Asp—Arg—Asn—Lys—Lys—Lys—Lys—Glu—Thr—Cys .

Peptide 2 is also favorable, but is clearly less favorable than Peptide 1 from the viewpoint of hydrophilicity as of its higher potential for spatial organization (probably as amphiphilic helix).

Finally, it will be noted that the C-terminal end constitutes a preferred region as a function of its mobility, but it nevertheless remains very hydrophobic. For example, the following peptide is contemplated:

(peptide 3)

Cys—Gly—Val—Ser—Gln—Ser—Pro—Leu—Val—Gln

Peptide 3 can be fixed in a specific manner by an N-terminal Cys in such a way as to reproduce its aspect on the protein.

The nucleotide sequences of hap gene encoding those peptides are as follows:

For peptide 1:
GTCAGGAATGACAGGAACAAGAAAAAGAAGGAGACTTCGAAGCAAGAATGC.

For peptide 2:
GGGGTCACTCAGTCACCACTCGTGCAA.

For peptide 3:
AATGACAGGAACAAGAAAAAGAAGGAGACT.

For peptide of amino acids 175-185:
GCTGAGTTGGACCATCTCACAGAGAAGATTCCGA.

The polypeptides of the invention can be injected in mice, and monoclonal and polyclonal antibodies can be obtained. Classical methods can be used for the preparation of hybridomas. The antibodies can be used to quantify the amount of human receptors produced by patients in order to correlate the pathological states of illness and quantity of receptors or the absence of such receptors.

The polypeptide of the invention can be used in a test kit for the quantification of retinoic acid present in the serum of a patient to carry out such a test, the following procedure can be carried out, for example.

The assay is based on the competition between radiolabeled and unlabeled retinoic acid for a fixed but limited number of binding sites on RAR molecules. Radiolabeled retinoic acid is added in excess to all assay tubes. In the absence of any unlabeled retinoic acid, all the receptor binding sites will be occupied by radioactive retinoic acid. If unlabeled retinoic acid is present in the fluid sample (blood, serum, or the like), it will compete with the radioactive species for the available binding sites. Using standards of known concentration, the binding of labeled at each point may be determined and a calibration curve can be constructed.

For example, the test can be performed in a microplate. RAR of a known centration are coated on the microplate. The sample fluid is added. An excess of labeled retinoic acid is then added in each well of the plate and the amount of labeled retinoic acid fixed on the receptors is quantified. All details of the steps of the procedure are known to those of ordinary skill in the art.

Epitope-bearing polypeptides, particularly those whose N-terminal and C-terminal amino acids are free, are accessible by chemical synthesis using techniques well known in the chemistry of proteins. For example, the synthesis of peptides in homogeneous solution and in solid phase is well known.

In this respect, recourse may be had to the solid phase synthesis of peptides using the method of Merrifield, J. Am. Chem. Assoc. 85, 2149–2154 (1964) or the method of synthesis in homogeneous solution described by Houbenweyl in the work entitled "Methoden der Organische Chemie" (Methods of Organic Chemistry), edited by E. WUNSCH, vol. 15-I and II, THIEME, Stuttgart (1974).

This method of synthesis consists of successively condensing either the successive amino acid in pairs in the appropriate order, or successive peptide fragments previously available or formed and containing already several aminoacyl residues in the appropriate order, respectively. Except for the carboxyl and amino groups which will be engaged in the formation of the peptide bonds, care must be taken to protect beforehand all other reactive groups borne by these aminoacyl groups and fragments. However, prior to the formation of the peptide bonds, the carboxyl groups are advantageously activated according to methods well known in the synthesis of peptides. Alternatively, recourse may be had to coupling reactions bringing into play conventional coupling reagents, for instance of the carbodiimide type such as 1-ethyl-3-(3-dimethyl-aminopropyl)-carbodiimide. When the amino acid group carries an additional amino group (e.g. lysine) or another acid function (e.g. glutamic acid), these groups may be protected by carbobenzoxy or t-butyloxycarbonyl groups, as regards the amino groups, or by t-butylester groups, as regards the carboxylic groups. Similar procedures are available for the protection of other reactive groups. For example, SH group (e.g. in cysteine) can be protected by an acetamidomethyl or paramethoxybenzyl group.

In the case of progressive synthesis, amino acid by amino acid, the synthesis preferably starts by the condensation of the C-terminal amino acid with the amino acid which corresponds to the neighboring aminoacyl group in the desired sequence and so on, step by step, up to the N-terminal amino acid. Another preferred technique that can be relied upon is that described by R. D. Merrifield in "Solid Phase Peptide Synthesis" (J. Am. Chem. Soc., 45, 2149-2154). In accordance with the Merrifield process, the first C-terminal amino acid of the chain is fixed to a suitable porous polymeric resin by means of its carboxylic group, the amino group of said amino acid then being protected, for example, by a t-butyloxycarbonyl group.

When the first C-terminal amino acid is thus fixed to the resin, the protective group of the amino group is removed by washing the resin with an acid, i.e. trifluoroacetic acid when the protective group of the amino group is a t-butyloxycarbonyl group.

Then the carboxylic group of the second amino acid, which is to provide the second aminoacyl group of the desired peptide sequence, is coupled to the deprotected amino group of the C-terminal amino acid fixed to the resin. Preferably, the carboxyl group of this second amino acid has been activated, for example by dicyclohexylcarbodiimide, while its amino group has been protected, for example by a t-butyloxycarbonyl group. The first part of the desired peptide chain, which comprises the first two amino acids, is thus obtained. As previously, the amino group is then deprotected, and one can further proceed with the fixing of the next aminoacyl group and so forth until the whole peptide sought is obtained.

The protective groups of the different side groups, if any, of the peptide chain so formed can then be removed. The peptide sought can then be detached from the resin, for exmple, by means of hydrofluoric acid, and finally recovered in pure form from the acid solution according to conventional procedures.

Depending on the use to be made of the proteins of the invention, it may be desirable to label the proteins. Examples of suitable labels are radioactive labels, enzymatic labels, flourescent labels, chemiluminescent labels, or chromophores. The methods for labeling proteins of the invention do not differ in essence from those widely used for labeling immunoglobulin.

A.3. Tissue Specific mRNA Distribution

In order to study expression of the hap gene, Northern blot analysis was performed using MNT as a probe and poly(A)+RNA extracted from various human tissues and cell lines. The results are shown in FIG. 3.

More particularly, Northern blot analyses were performed with poly(A)+RNAs (15 μg per lane) extracted from different human organs and cell lines. A control hybridization with a mouse beta-actin cDNA probe is shown below the hybridizations in FIG. 3. Hap mRNA in different tissues is shown in FIG. 4A as follows:
Lane a ovary
Lane b uterus
Lane c HBL 100 mammary cells
Lane d adult spleen
Lane e 18 weeks fetal spleen
Lane f K562
Lane g HL60 hematopoeitic cell lines
Lane h prostatic adenoma
Lane 1 kidney
Lane j adult liver
Lane k 18 weeks fetal liver.
Lanes a-k correspond to a one day exposure.

Figure 3:
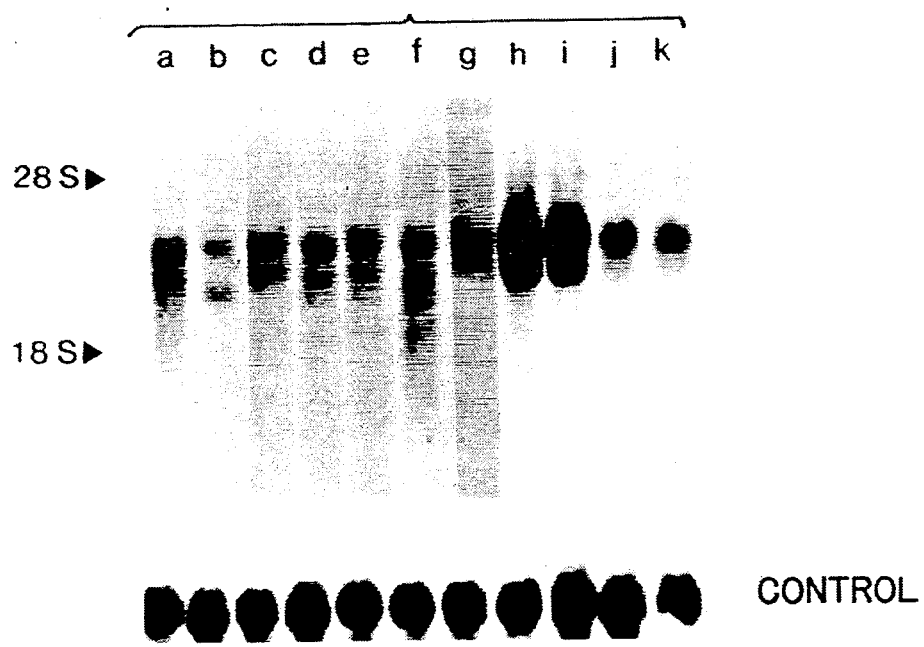
FIG. 3 depicts the distribution of hap mRNA in different tissues as determined by Northern blot analysis.

FIG. 3 shows that two RNA species of 3 kb and +2.5 kb (the size of this smaller mRNA is slightly variable from one organ to another) were expressed at low abundance in ovary (lane a), uterus (lane b), HBL 100 mammary cells (lane c), adult and fetal spleen (lane d and e, respectively), and K562 and HL60 hematopoeitic cell lines (lanes f and g, respectively). Surprisingly, an approximately tenfold higher level of expression was detected in prostatic adenoma (lane h) and kidney (lane i). By contrast, a single mRNA of 3000 nucleotides, expressed at low levels, was present in poly(A)+RNA from adult and fetal liver tissues (lanes j and k). Therefore, the cloned hap cDNA is likely to be a full-length copy of this transcript.

The finding of two mRNA species overexpressed in prostate and kidney, as well as the presence of a single mRNA expressed at low level in adult and fetal livers show that hap expression is differentially regulated in those organs. This tissue specific expression provides some indication that prostate and kidney, as well as liver, could be key tissues and that hap functions in those cell types may differ.

Figure 4:
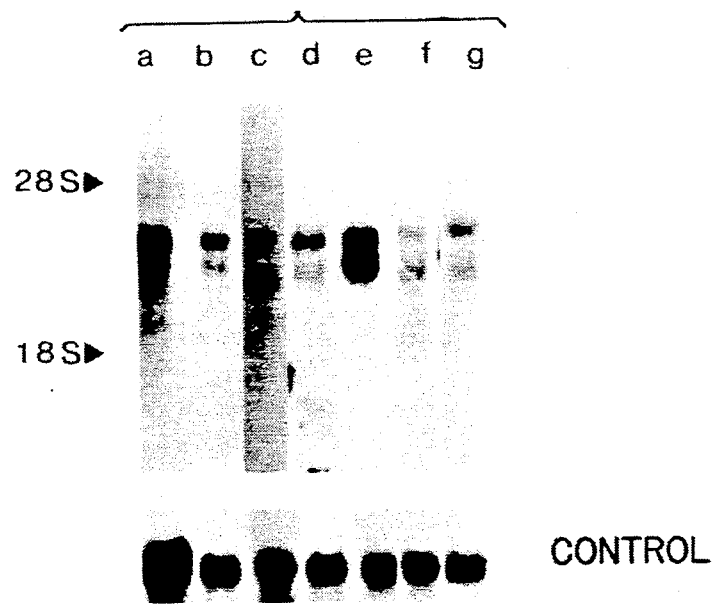
FIG. 4 depicts the distribution of hap mRNA in HCC and HCC derived cell lines as determined by Northern blot analysis.

FIG. 4 shows hap mRNA in HCC and HCC derived cell-lines as follows:
Lane a, normal liver (four days autoradiography);
Lanes b, c, d: three HCC samples (Lane b, patient Ca; Lane c, patient Mo; Lane d, patient TCl );
Lanes e, f, g: three HCC-derived cell lines (Lane e, PLC/PRF/5; Lane f, HEPG2; Lane g, HEP 3B).
The lanes b–g correspond to a one day exposure. Once again, a control hybridization with a normal beta-actin cDNA probe is shown below the hybridizations.

With reference to FIG. 4, the smaller 2.5 kb mRNA was undetectable, even after long exposure, in three adult and two fetal human livers analyzed (FIG. 4, Lane a). This differential expression in normal livers may suggest a distinct role of hap in this particular tissue.

Northern blot analysis of human HCCs and hepatoma cell lines showed almost constant alterations in hap transcription. There are two possible alternatives to explain this result. The smaller mRNA species can be simply expressed as a consequence of the cellular dedifferentiation. The tumorous liver cell, having lost its differentiated characteristics, would behave as any other cell type and thus express the same 2.5 kb mRNA as found in non-hepatic cells. However, the inability to detect such a smaller transcript in fetal livers does not seem to favor this hypothesis. On the contrary, the presence of the smaller transcript may have preceded the tumorigenesis events and would rather reflect a preneoplastic state. The presence of an inappropriately expressed hap protein, normally absent from normal hepatocytes, may have directly participated to the hepatocellular transformation. In this respect, the previous study reporting a HBV integration in the hap gene of a human HCC (Dejean et al., 1986) strongly supports the idea that hap could be causatively involved in liver oncogenesis. Indeed, in this tumor, a chimeric gene between the viral pre-S1 gene and hap may have resulted in the over-expression of a truncated hap protein. At present, it is the one found in non-hepatic tissues.

A.4. Expression of hap in Hepatocellular Carcinoma

Hap was first identified in a human primary liver cancer. Encouraged by this finding, poly(A)+RNA from seven hepatoma and hepatoma-derived cell lines were analyzed by Northern-blotting. Five of them contained integrated HBV DNA sequences. In addition to the 3 kb long mRNA found in normal adult and fetal liver, an additional +2.5 kb RNA species was observed, in equal or even greater amount, in three out of four HCC (FIG. 4, Lanes b, c, d) and in the PLC/PRF/5, HEPG2 and HEP3B hepatoma cell-lines (Lanes e, f, g). The size of the smaller transcript was variable from sample to sample. In addition, the two transcripts were strikingly overexpressed, at least ten fold, in the PLC/PRF/5 cells.

To test the possibility that the inappropriate expression of hap in those six tumors and tumorous cell-lines might be the consequence of a genomic DNA alteration, Southern-blotting of cellular DNA was performed using, as two probes, the MNT fragment together with a 1 kb EcoRI fragment corresponding to the 5' extremity of the cDNA insert (FIG. 2). No rearrangement and/or amplification was detected with any of these two probes which detect a different single exon (data not shown), suggesting that the hap gene was not altered at the genomic level. It is yet unknown whether the +2.5 kb mRNA, present in the liver tumorous samples and cell lines, corresponds to the same smaller transcript as that found in non-hepatic tissues. However, its presence in the liver seems to be clearly associated to the hepatocellular transformed state.

A.5. Hormone-binding Assay

Amino-acid homologies between the hap protein and the c-erbA/steroid receptors support the hypothesis that hap may be a receptor for a thyroid/steroid hormone-related ligand. The ability to express functional receptors in vitro from cloned c-erbA/steroid receptor genes led to the use of an in vitro translation assay to identify a putative hap ligand.

Figure 5:
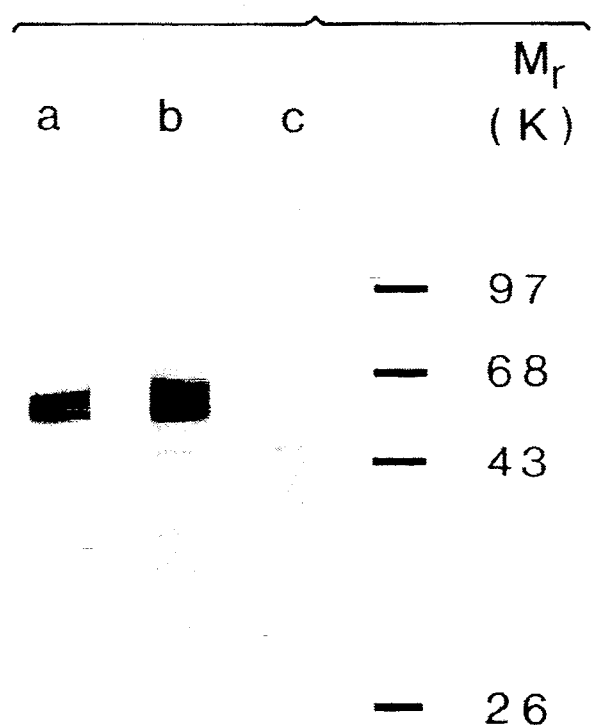
FIG. 5 is a fluorograph of hap polypeptide synthesized in vitro and isolated on SDS-polyacrylamide gel.

The coding region of hap was cloned into pTZ18 plasmid vector to allow in vitro transcription in reticulocyte lysates. The results are shown in FIG. 5. More particularly, $^{35}$S-methionine-labelled products synthesized using T7 polymerase-catalysed RNA transcripts were separated on a 12% SDS-polyacrylamide gel, which was fluorographed (DMSO-PPO). The lanes in FIG. 5 are as follows:

Lane a, pCOD 20 (sense RNA, 70 ng)
Lane b, pCOD 20 (140 ng)
Lane c, pCOD 14 (antisense RNA, 140 ng).

FIG. 5 shows that the hap RNA directed the efficient synthesis of a major protein, with a 51K relative molecular mass, consistent with the size predicted by the amino acid sequence (lanes a and b), whereas the antisense RNA-programmed lysate gave negligible incorporation (lane c).

Because c-erbA and hap colocalize on chromosome 3 and are more closely related according to their amino acid sequence, ($^{125}$I)-T3 (triiodothyronine), -reverse T3 (3,3',5'-triiodothyronine) and -T4 (thyroxine), were first tested for their binding with the in vitro translated hap polypeptide. No specific fixation with any of those three thyroid hormones could be detected. As a positive control, binding of a T3 was detected with nuclear extracts from HeLa cells. The results were negative as well when the experiment was repeated with (3H)-retinol, -retinoic acid, and -testosterone, which represent three putative ligands for hap whose receptors have not yet been cloned. Although it cannot excluded that hap may encode a hormone independent transcriptional activator, it is more likely that hap product, i.e. the hap protein, is a receptor for a presently unidentified hormone.

A.6. Similarity of HAP Protein to Thyroid/Steroid Hormone Receptors

The c-erbA gene product, recently identified as a receptor for thyroid hormone (Weinberger, et al., 1986; Sap et al., 1986), as well as the steroid receptors, belong to a superfamily of regulatory proteins, which consequently to their binding with specific ligand, appear capable of activating the transcription of target genes (reviewed by Yamamoto, 1985). This activation seems to be the result of a specific binding of the hormone-receptor complex to high-affinity sites on chromatin.

Comparative sequence analysis has been made between the following different cloned steroid receptors:

glucocorticoid receptor (GR) (Hollenberg et al., 1985; Miesfeld et al., 1986);

oestrogen receptor (ER) (Green et al., 1986; Greene et al., 1986);

progesterone receptor (PR) (Conneely et al., 1986; Loosfelt et al., 1986); and thyroid hormone receptor (c-erbA product) (Weinberger et al., 1986; Sap et al., 1986).

Mutation analysis has also been carried out. (Kumar et al., 1986; Hollenberg et al., 1987; Miesfeld et al., 1987). The results revealed the presence of two conserved regions representing the putative DNA-binding and hormone-binding domains of those molecules. It has now been discovered that hap protein is homologous to the thyroid/steroid hormone receptors.

Figure 6:
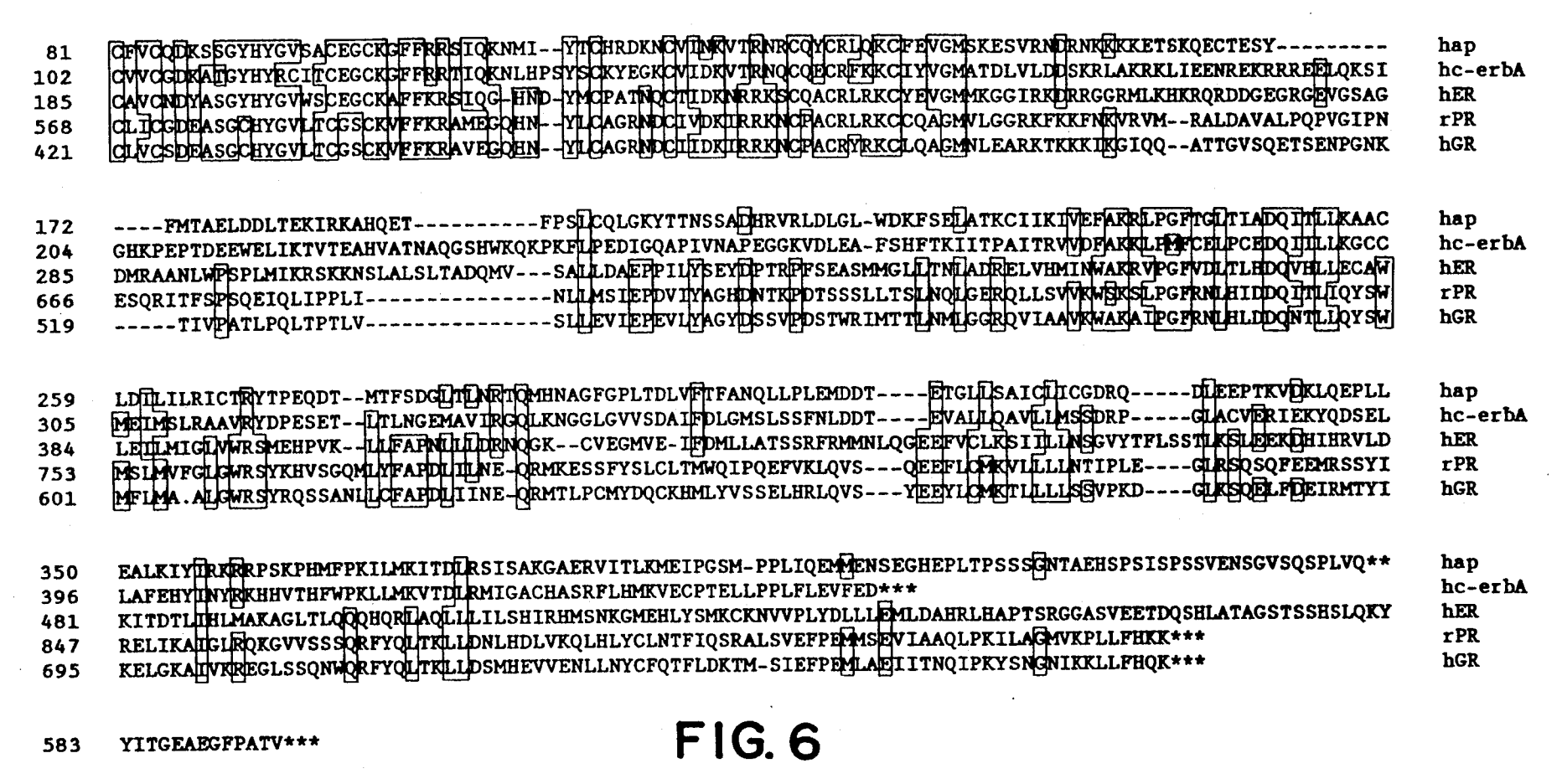

More particularly, homology previously reported between the putative 147 bp cellular exon (bracketed in FIG. 2) and the c-erbA/steroid receptor genes led us to compare the entire hap predicted amino acid sequence with hGR, hPR, hER, and hc-erbA/thyroid hormone receptor. The five sequences have been aligned for maximal homology by the introduction of gaps. The results are depicted in FIG. 6. Specifically, the following nucleotide sequences were aligned after a computer alignment of pairs (Wilbur and Lipman, 1983):

hap product, human placenta c-erbA protein (hc-erbA, Weinberger et al., 1986), human oestrogen receptor (hER, Green et al., 1986), rabbit progesterone receptor (rPR, Loosfelt et al., 1986), and human glucocorticoid receptor (hGR, Hollenberg et al., 1985).

A minimal number of gaps (—) was introduced in the alignment.

Amino acid residues matched in at least three of the polypeptides are boxed in FIG. 6. The codes for amino acids are:

| | | |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |

| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tyrptophan |
| Y | Tyr | Tyrosine |

The sequence comparison analysis revealed that the two regions highly conserved in the thyroid/steroid hormone receptors are similarly conserved in the hap product. Consequently, the overall organization of hap is much similar to that of the four receptors in that it can be roughly divided into four regions (arbitrarily referred to as A/B, C, D and E (Krust et al., 1986)).

In C, the most highly conserved region, extending from amino-acid 81 to 146 in hap, the nine cysteines already conserved between the four known receptors are strikingly present at the same positions. Comparison between the cysteine-rich region of hap with the corresponding region of the four receptors reveals 64% amino acid identity with hc-erbA, 59% with hER, 42% with rPR and 44% with hGR. This is schematically represented in FIG. 7.

Referring to FIG. 7, a schematic alignment of the five proteins can be seen. The division of the thyroid/steroid hormone receptor regions A/B, C, D, E is schematically represented in the hap protein. The two highly conserved regions, identified as the putative DNA-binding (region C) and hormone-binding (region E) domains of the receptors, are shown as stippled blocks. The numbers refer to the position of amino acid residues. The sequences of each of the hc-erbA product, hER, rPR and hGR receptors are compared with the hap protein. The numbers present in the stippled blocks correspond to the percentage of homology between hap protein on the one hand and each of the receptors on the other hand in the two highly conserved regions C and E. The empty blocks correspond to the non-conserved A/B and D regions.

It has also been found that hap shares 47% homology in the C region with the chicken vitamin D3 receptor (VDR), recently cloned as a partial cDNA (McDonnel et al., 1987) (data not shown). Apart from c-erbA, which contains two additional residues, the 66 amino acid long C region shows a constant length in hER, VDR, hGR, rPR and hap sequences.

Region E (residue 195-448), which is well-conserved, but to a lesser extent, shows a slightly stronger homology to hc-erbA (38%) (FIG. 7). The hap/hc-erbA homology, however, remains inferior to the identity found between hGR and rPR (90 and 51 percent in regions C and E, respectively). No significant homology was observed when comparing the A/B (residue 1-80) and D (147-194) regions which are similarly variable, both in sequence and length, in the four known receptors.

It is thus evident from FIGS. 6 and 7 that the hap product exhibits two highly homologous regions. The C domain is characterized by strikingly conserved Cys-X2-Cys units, evoking those found in the DNA-binding transcriptional factor TFIIIA (Miller et al., 1985) and in some protein that regulated development, such as Kruppel (Rosenberg et al., 1986). In the latter, the Cys-X2-Cys, together with His -X3-His units, can form metal binding fingers that are crucial for DNA-binding (Berg, 1986; Diakun et al., 1986). Similarly, the C domain of previously cloned receptors are likely to contain metal binding fingers and were shown to bind DNA (Hollenberg et al., 1987; Miesfeld et al., 1987). Since the C region of the hap gene product shares 24/66 conserved amino acids with all steroid or thyroid hormone receptors, including all nine cysteine residues, it is likely that the hap protein is a DNA-binding protein. Hap, as c-erbA/steroid receptors, may modulate the transcription of target genes.

In addition, the significant homology detected in the E domain suggests that hap product is a ligand-binding protein and directs the question of the nature of the putative ligand. Hap protein seems to differ too much from previously cloned hormone receptors to be a variant of one of them. In addition, the in vitro translated 51K hap polypeptide failed to bind all ligands tested. Although that hap gene product could be a ligand-independent DNA-binding protein, it is believed that hap encodes a receptor for a presently unidentified circulating or intracellular ligand.

It has been proposed that steroid and thyroid hormone receptor genes were derived from a common ancestor (Green and Chambon, 1986). This primordial gene may have provided to the receptors their common scaffolding while the hormone and target gene cellular DNA specificities were acquired through mutations accumulated in the C and E domains. Hap is both linked to the steroid receptor gene by its shorter C domain (66AA) and to the thyroid hormone receptor genes by its clearly greater homology with c-erbA in the E region (38%). This suggests that hap ligand may belong to a different hormone family.

Different functions have been assigned to the four regions defined in the glucocorticoid and oestrogen receptors (Kumar et al., 1986; Giguere et al., 1986; Miesfeld et al., 1987). By analogy, the regions C and E may represent, respectively, the putative DNA-binding and hormone-binding domains of the hap protein. The precise functions of the A/B and D domains remain unknown. The presence of the amino-terminal A/B region of the human GR has been recently shown to be necessary for full transcriptional activity (Hollenberg et al., 1987), whereas results obtained with the rat GR indicated it was dispensable (Miesfeld et al., 1987). From this alignment study it appears that hap is distinct, but closely related to the thyroid/steroid hormone receptor genes suggesting that its product may be a novel ligand-dependent, DNA-binding protein.

A.7. Hap Related Genes

Southern blotting was performed on restriction enzyme-digested DNAs obtained from different organisms with labelled genomic MNT fragment containing the first exon of the cysteine-rich region of hap. The results are shown in FIG. 8. More particularly, hap related genes in vertebrates (A) and in humans (B and C) were compared. Cellular DNA (20 μg) from various sources was digested with BglII and subjected to Southern blot analysis using the MNT probe under non-stringent hybridization and washing conditions. The lanes in FIG. 8A are identified as follows:

Lane a human liver
Lane b domestic dog liver
Lane c woodchuck (marmota monax)
Lane d mouse liver (BALB/c strain)

Lane e chicken erythrocytes
Lane f cartilaginous fish (Torpedo).

Figure 8A:
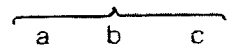
FIG. 8 depicts hap related genes in vertebrates (A) and in humans (B and C) as determined by Southern blot analysis.

As illustrated in FIG. 8A, BglII fragments that anneal effectively with MNT probe under non-stringent hybridization and washing conditions are present in digests of DNA from several mammals (mouse, woodchuck, dog) as well as from bird and fish. If this blotting experiment is performed at high stringency, no hybridization is observed with heterologous DNA (data not shown). These data suggest that the hybridizing sequences represent evolutionarily conserved homologs of hap.

Figure 8B:
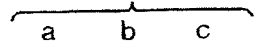

The existence of multiple c-erbA and GR genes (Jansson et al., 1983; Weinberger et al., 1986; Hollenberg et al., 1985) encouraged a search for hap related genes in the human genome. Thus, human liver DNA digested by PstI, BamHI, and EcoRI was analyzed by Southern blot, using the MNT probe, under stringent conditions. The results are shown in FIG. 8B. After digestion of liver DNA by PstI (lane a), BamHI (lane b), or EcoRI (lane c), a single band is observed with the MNT probe in high stringency hybridization.

Figure 8C:

The same blot was hybridized with the MNT probe under non-stringent hybridization and washing conditions. The results are shown in FIG. 8C. When Southern blotting was performed under relaxed hybridization conditions, additional bands were observed in the products of each enzyme digestion (FIG. 8C, lanes a, b, c). For example, seven faint hybridizing fragments of 1, 1.7, 2.4, 3.8, 5.5, 6, 7.4 kb were observed in the BamHI digestion (lane b). None of those bands cross-hybridized with a human c-erbA probe (data not shown). A minimum of three faint bands in the PstI lane suggests the existence of at least four related hap genes in the human genome.

From a panel of somatic cell hybrids, hap was assigned to chromosome 3 (Dejean et al., 1986). To find out whether the hap related genes were all chromosomally linked or not, DNAs from human liver LA.56U and 53K cell-lines (two mouse/human somatic cell hybrids containing, altogether, most human chromosomes except chromosome 3 (Nguyen Van Cong et al., 1986)), and mouse lymphoid cells were BamHI digested, transferred to nitrocellulose, and hybridized to the MNT probe in low-stringency conditions. Of the seven faint bands present in the human liver DNA track, two at least were conserved in the LA.56U and/or L.53K cell lines DNAs digestion (data not shown) indicating that some of the hap genes do not localize on chromosome 3. Altogether the results suggest that hap belongs to a multigene family consisting of at least four members dispersed in the human genome.

The experimental procedures used in carrying out this invention will now be described in greater detail.

A.8. Experimental Procedures

A.8.1. cDNA Cloning and Screening

Briefly, the cDNA was synthesized using oligo dT primed poly-A+liver mRNA, using the method of Gubler and Hoffman (1983) (C. de Taisne, unpublished data). cDNA's were size selected on a sucrose gradient and the fraction corresponding to a mean size of 3 kb was treated with EcoRI methylase. After addition of EcoRI linkers, the cDNA was digested by EcoRI and ligated to an EcoRI restricted lambda-NM1149. After in vitro encapsidation, the phages were amplified on C600 hfl and $2 \times 10^6$ recombinant were plated at a density of 10,000 per dish. The dishes were transferred to nylon filters and hybridized to the 350 bp EcoRI-EcoRI genomic fragment (MNT) previously described (Dejean et al., 1986). Four positive clones were isolated and the restriction map of each insert was determined. The longest one, clone lambda-13, was subjected to nucleotide sequence analysis.

A.8.2. Nucleotide Sequence

Clone lambda-13 DNA was sonicated, treated with the Klenow fragment of DNA polymerase plus deoxyribonucleotides (2 h, 15° C.) and fractionated by agarose gel electrophoresis. Fragments of 400–700 bp were excised and electroeluted. DNA was ethanol-precipitated, ligated to dephosphorylated SmaI cleaved M13 mp8 replication form DNA and transfected into *Excherichia coli* strain TG-1 by the high-efficiency technique of Hanahan (1983). Recombinant clones were detected by plaque hybridization using either of the four EcoRI fragments of cDNA insert as probes (FIG. 1). Single-stranded templates were prepared from plaques exhibiting positive hybridization signals and were sequenced by the dideoxy chain termination procedure (Sanger et al., 1977) using buffer gradient gels (Biggin et al., 1983).

A.8.3. Northern Blot

Cytoplasmic RNA was isolated from the fresh tissue using guanidine thiocyanate, and the RNA cell line was extracted using isotonic buffer and 0.5% SDS, 10 mn Na acetate pH 5.2. RNAs were then treated with hot phenol. Poly(A)+RNA (15 µg) of the different samples were separated on a 1% agarose gel containing glyoxal, transfered to nylon filters and probed using the nick-translated MNT fragment. The experimental procedure is described in Maniatis et al. (1982).

A.8.4. Southern Blot

20 µg of genomic DNA was digested to completion, fractionated on a 0.8% agarose gel and transfered to nylon paper. Low stringency hybridization was performed as follows: 24 h prehybridization in 35% formamide, 5×Denhardt, 5×SSC, 300 µg/ml denatured salmon sperm DNA, at 40° C.; 48 h hybridization with 35% formamide, 5×Denhardt, 5×SSC, 10% Dextran sulfate, $2 \times 10^6$ cpm/ml denatured $^{32}$P labelled DNA probe (specific activity $5 \times 10^8$ cpm/µg). Washes were made in 2×SSC, 0.1 SDS, 55° C. for 15 min. High stringency hybridization conditions were the same except that 50% formamide was used with 24 h hybridization. Washing was in 0.1×SSC, 0.1 SDS, 55° C. for 30 min.

A.8.5. Construction of Plasmids for In-Vitro Translation

The 3 kb insert of phage lambda-13 was excised from the phage DNA by partial EcoRI digestion, electroeluted and digested by BamHI and HindIII. To remove most of the untranslated sequences, the 1.8 kb cDNA fragment obtained was then partially digested by MaeI (Boehringer). The 1.4 kb MaeI-MaeI fragment, extending from the first to the third MaeI site in the cDNA insert sequence (FIG. 1) and containing the complete coding region was mixed with SmaI cut dephosphorylated pTZ18 (Pharmacia), the extremities were filled in using Kleenow fragment of DNA PolI (Amersham) and ligated. Two plasmids were derived: pCOD20 (sense) and pCOD14 (antisense).

A.8.6. Translation and hormone binding assays pCOD20 and pCOD14 were linearized with HindIII. Capped mRNA was generated using 5 µg of DNA, 5 uM rNTP, 25 mM DTT, 100 U RNAsin (Promega), 50 U T7 Pol (Genofit) in 40 mM Tris pH 8, 8 mM $MgCl_2$, 2 mM spermidine, 50 mM NaCl, in 100 μl at 37° C. Capping was performed by omitting GTP and adding CAP (m$^7$ G (5') ppp (5') G) (Pharmacia) for the 15 first minutes of the reaction. Translation was performed using rabbit reticulocyte lysate (Amersham) under the suggested conditions using 40 μl of lystae for 2.5 μg of capped RNA.

The thyroid hormone binding assays included 5 ul of lysate in (0.25M sucrose, 0.25 KCl, 20 mM Tris (pH 7.5), 1 mM MgCl$_2$, 2 mM EDTA, 5 mM DTT) with 1 mM $^{125}$I T4, $^{125}$I T3 or $^{125}$I rT3 (specific activity: T4, rT3 1400 mCi/mg Amersham, T3 3000 mCi/mg NEN). After at least 2 h of incubation at 0° C., free was separated from bound by filtration through millipore HAWP 02500 filters using 10 ml of ice cold buffer. For testosterone, retinol, retinoic acid 10 ul of lysate were added to 45 lambda of 20 mM Tris pH 7.3, 1 mM EDTA, 50 mM NaCl, 2 mM beta-mercaptoethanol and 5 mM testosterone, 400 mM retinol or 15 mM retinoic acid (81 Ci/mmol; 60 Ci/mmol; 46 Ci/mmol; Amersham). After an overnight incubation at 0° C. free was separated from bound by Dextran coated charcoal (0.5% Norit A-0.05% T70) and centrifugation. All experiments were performed in duplicates and parallel experiments were performed with 100 fold excess corresponding cold hormone.

B. Identification of a Hap Protein as a Second Human Retinoic Acid Receptor

The hap protein (hap for hepatoma) exhibits strong homology with the human retinoic acid receptor (RAR), de Thé et al. (1987), Petkovich et al. (1987), which has been recently characterized Petkovich et al. (1987), Giguere et al. (1987). To test the possibility that the hap protein might also be a retinoid receptor, a chimaeric receptor was created by replacing the putative DNA binding domain of hap with that of the human oestrogen receptor (ER). The resulting hap-ER chimaera was then tested for its ability to trans-activate an oestrogen-responsive reporter gene (vit-tk-CAT) in the presence of possible receptor ligands. It was discovered that retinoic acid (RA) at physiological concentrations is effective in inducing the expression of this reporter gene by the hap-ER chimaeric receptor. This demonstrates the existence of two human retinoic acid receptors designated RAR-α and RAR-β.

More particularly, it has been discovered that the hap protein is a second retinoic acid receptor. Thus, the expression "hap protein" is used interchangeably herein with the abbreviation "RAR-β" for the human retinoic acid receptor.

Figure 9A:
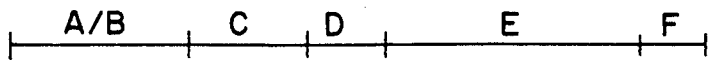
FIG. 9(a) identifies six regions, A-F, of RAR-α and RAR-β, by analogy with oestrogen receptors.
Figure 9B:
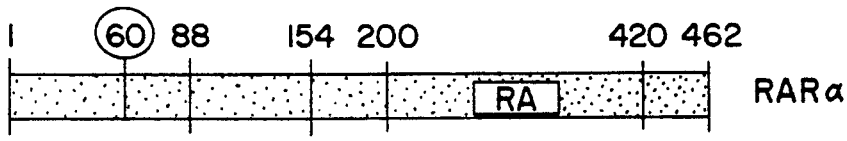
FIGS. 9(b) and 9(c) are schematic representations of RAR-α and RAR-β with the percent homology (% amino acid identity) shown between the FIGS.

Referring to FIG. 9(a), (b), and (c), a schematic representation of the homology between RAR-α and RAR-β is shown. FIG. 9, (a-c) shows a schematic comparison of the cDNA-deduced amino-acid sequences of RAR, Petkovich et al. (1987), Giguere et al. (1987), and hap, de Thé et al. (1987), proteins (hereafter also referred to as RAR-α and RAR-β, respectively). In agreement with the report of Giguere et al. (1987), RAR-α, FIG. 9(b), is represented as a 462 amino acid long protein (that is, 30 amino acids longer at the N-terminus in the report of Petkovich et al. (1987). It has been found (unpublished results) that the sequences of the RAR-α cDNA clones in the previous report of Giguere et al. (1987) were not colinear with the corresponding genomic sequence upstream of the initiating AUG. In contrast, perfect colinearity exists between the 5' terminal region of the cDNA sequence of Giguere et al. (1987) and our genomic sequence, substantiating their characterization of the open reading frame (ORF) of RAR-α cDNA.

Figure 9C:
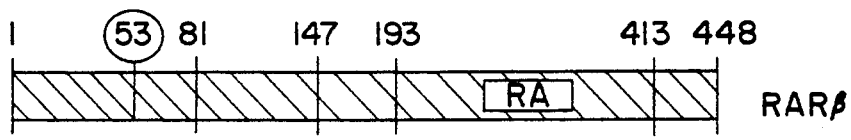

The receptors RAR-α, FIG. 9(b), and RAR-β, FIG. 9(c), are divided into six regions, A-F (see FIG. 9(a)), by analogy with oestrogen receptors (see infra). Numbers in FIG. 9 denote amino acid positions. The circled numbers mark the positions of one exon junction, determined from genomic DNA sequence for RAR-α (Petkovich et al. (1987) and unpublished data of the Strasbourg laboratory) and RAR-β Dejean et al. (1986). Region E comprises the putative RA binding domain for each receptor. The degree of homology between the receptors is shown between FIG. 9(b) and FIG. 9(c) (% amino-acid identity).

More particularly, when RAR-α and RAR-β are divided into the five regions analogous to the A/B, C, D, E, and F regions of other members of the nuclear receptor family, (Krust et al. (1986) and Green et al. (1986)), FIG. 9(a), the highest degree of homology (97% amino acid identity) is found within the 66 residue region C, which in the case of the human glucocorticoid (hGR) and oestrogen (hER) receptors was identified as the DNA-binding domain responsible for the specific recognition of the cognate hormone-responsive elements (Green et al. (1987), Kuman et al. (1987), Hollenberg et al. (1987), and Ruscoui et al. (1987) and refs. therein). The next most highly conserved region, E (90% amino acid identity), is a stretch of 220 amino acids, which is homologous to the ligand binding domain of the steroid hormone receptors and appears to contain the RA binding domain of RAR-α (Petkovich et al. (1987) refs. therein). Regions C and E are linked by a 46-residue hydrophilic region, D, which is 74% homologous between RAR-α and RAR-β.

In contrast, the carboxy-terminal (F) and amino-terminal (A/B) portions of the receptors are much less similar (ca 22% and 37% amino acid identity, respectively) and differ in length. A closer comparison of the A/B regions shows that residues 60-87 of RAR-α and 53-80 of RAR-β are 79% identical, whereas there is no significant homology within the remainder of the A/B region. Note in this respect that genomic DNA sequence analyses have located exon boundaries between residues 59/60 of RAR-α, Petkovich et al. (1987), and residues 52/53 of RAR-β, Dejean et al. (1986).

Regions of RAR-β of particular interest in this invention are the N-terminal region comprising amino acids 1 to 53 and the C-terminal region comprising amino acids 413 to 448. These two regions (1-53 and 413-448) are the most specific for RAR-β, showing only 15% and 22% homology, respectively, with RAR-α. Also of interest are the DNA sequences encoding these amino acids. These amino acid sequences and DNA sequences can be employed in assays specific for RAR-β and its messenger RNA.

These structural homologies suggested that, like RAR-α, RAR-β might be a retinoid-inducible transcription factor. To test this hypothesis, a chimaeric receptor was constructed between RAR-β and the human oestrogen receptor, RAR-β-ER.CAS, in a similar experiment to that used to demonstrate that RAR-α encodes a receptor for retinoic acid (RA), Petkovich et al. (1987), Green et al. (1988). The chimaeric receptor RAR-β-ER.CAS is shown in FIG. 9(f).

Figure 9D:
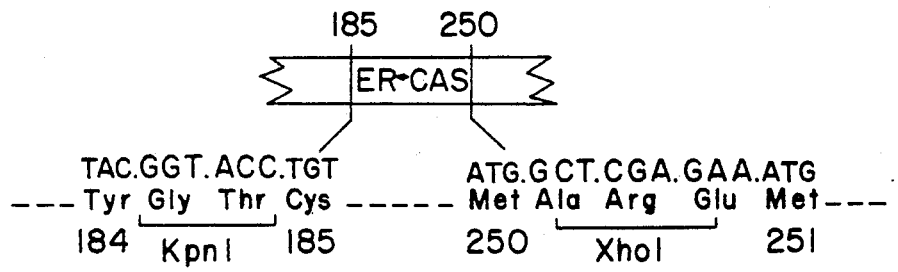
FIG. 9(d) is a schematic representation of the oestrogen receptor DNA-binding cassette ER.CAS.

The oestrogen receptor DNA-binding cassette, ER.-CAS, is schematically shown in FIG. 9(d). It is derived from the hER construct HE28, Green et al. (1987), and comprises the hER C-region (residues 185–205), flanked by unique restriction enzyme sites for KpnI (5') and XhoI (3'). The corresponding sites were engineered on either side of region C of both a truncated form of RAR-α, Petkovich et al. (1987), and RAR-β, allowing replacement of those regions by ER.CAS. This resulted in the creation of the chimaeric receptor RAR-α-ER.CAS, which is schematically shown in FIG. 9(e), and the chimaeric receptor RAR-β-ER.CAS, which is schematically shown in FIG. 9(f).

Figure 9E:
FIGS. 9(e) and 9(f) are schematic representations of the chimaeric receptors RAR-α-ER.CAS and RAR-β-ER.CAS, respectively.
Figure 9F:

More particularly, the construction of RAR-α-ER.CAS of FIG. 9(e) has been described by Petkovich et al. (1987). RAR-β-ER.CAS was assembled as follows. A 1.4 kilobase DNA fragment containing the entire RAR-β ORF was isolated from a partial digest of the clone λ13, de Thé et al. (1987), with MaeI. The protruding ends were filled in with Klenow polymerase and the fragment was ligated initially into the SmaI site of pTZ18U (United States Biochemicals), yielding the plasmid pCOD20, de Thé et al. (1987). For mutagenesis and expression studies, the insert was excized from pCOD20 by total digestion with BamHI and partial digestion with EcoRI, and re-inserted into the EcoRI and BamHI sites of the expression vector pSG5, Green et al. (1988), yielding RAR-β0, which can be used to express RAR-β in vivo and in vitro. Using oligonucleotide-directed mutagenesis as described for RAR-α, Petkovich et al. (1987), KpnI and XhoI sites flanking region C (codons 81–146) were created in RAR-β0, whereas the XhoI site present in the A/B region was removed by mutation. RAR-β region C was then excized and replaced by the ER.CAS, giving the chimaeric receptor RAR-β-ER.CAS shown schematically in FIG. 9(f).

To test the efficacy of various ligands to activate the chimaeric receptor, HeLa cells were co-transfected with RAR-β-ER.CAS and a reporter gene containing the oestrogen-responsive upstream sequence of Xenopus vitellogenin A2 gene ERE (vit) linked to the herpes simplex virus thymidine kinase (tk) promoter and the Escherichia coli chloramphenicol acetyltransferase gene (CAT) (vit-tk-CAT, Green et al. (1987)).

More particularly, CAT activity resulting from activation of the reporter gene vit-tk-CAT by the chimaeric receptors RAR-α-ER.CAS and RAR-β-ER.CAS in the presence of RA is shown in FIG. 10(a). From 0–1,000 ng of RAR-α-ER.CAS or RAR-β-ER.CAS, together with vit-tk-CAT, were transfected into HeLa cells which were subsequently treated with $10^{-7}$M RA. Transfection experiments were as described by Petkovich et al. (1987). In the experiments reported in FIG. 10(a), 2 μg of vit-tk-CAT reporter DNA, 2 μg of the β-galactosidase expression plasmid pCH110 (Pharmacia), and the indicated amounts of the RAR-α or RAR-β chimaeric DNA (plus 16 μg of carrier plasmid DNA) were transfected into HeLa cells. Aliquots of extracts prepared from the transfected cells and corresponding to 1 OD unit of β-galactosidase activity were assayed for CAT activity as previously described by Petkovich et al. (1987).

FIG. 10(b) shows the effect of RA concentration on the induction of CAT activity by either RAR-α-ER.CAS or RAR-β-ER.CAS. Transfections were as in FIG. 10(a), but HeLa cells were transfected with 30 ng of either RAR-α-ER.CAS or RAR-β-ER.CAS along with 2 μg of both vit-tk-CAT and β-galactosidase control plasmid pCH110 (see above) and then treated with the indicated concentrations of RA or retinol.

Figure 10C:
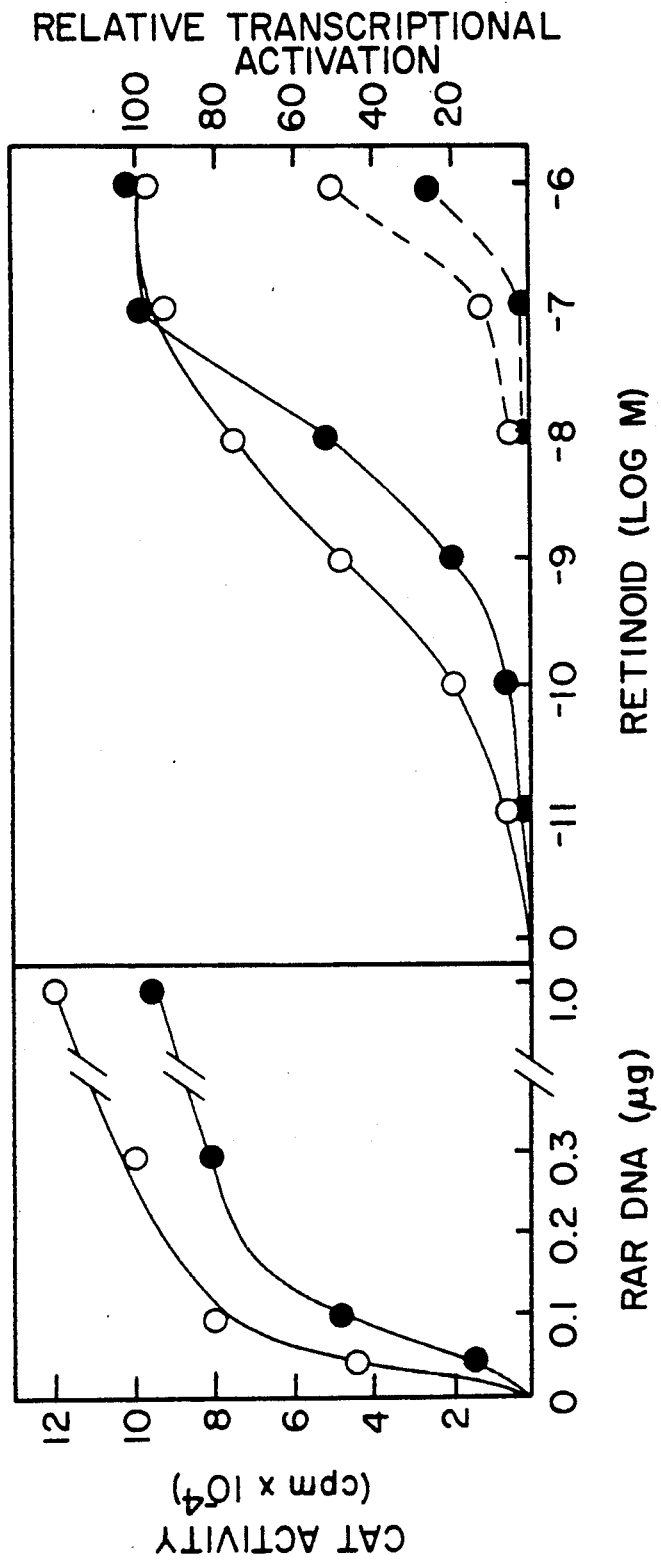
FIG. 10(c), left panel, shows trans-activation of vit-tk-CAT by increasing concentrations of RAR-α-

In FIG. 10(c), left panel, trans-activation of vit-tk-CAT by increasing concentrations of RAR-α-ER.CAS (solid circles) or RAR-β-ER.CAS (open circles) is shown. Experiments were similar to those described under FIG. 10(a), except that acetylated forms of $^{14}$C-chloramphenicol were isolated from thin-layer chromatography plates and their radioactivities determined by scintillation counting.

FIG. 10(c), right panel, is a graph of the results shown in FIG. 10(b) for RAR-α-ER.CAS (solid circles) and RAR-β-ER.CAS (open circles) in response to RA (solid line) or retinol (broken line). Experiments were performed as in FIG. 10(b), except that the acetylated forms of $^{14}$C-chloramphenicol were isolated, quantified by scintillation counting, and the results expressed in percent of maximal activation. The results displayed in both left and right panels of FIG. 10(c) are representative of several independent transfection experiments which gave identical results within 10% variation.

Addition to the culture medium of $10^{-7}$M of either thyroid hormone (T3 or T4), vitamin D3 [1.25(OH)$_2$D3], testosterone, or oestradiol did not result in any stimulation of vit-tk-CAT expression by RAR-β-ER.CAS (data not shown). In contrast, a strong stimulation of CAT activity was observed in the presence of $10^{-7}$M RA, whereas a much weaker stimulation was achieved with the same concentration of retinol (FIG. 10 and data not shown). The extent of stimulation increased with increasing amounts of transfected RAR-β-ER.CAS with a maximum stimulation of at least 50-fold (FIGS. 10(a) and 10(c), left panel). This stimulation was similar to that obtained in transfection experiments where the previously described RAR-α chimaeric receptor, RAR-α-ER.CAS, was used to stimulate vit-tk-CAT expression, Petkovich et al. (1987). No increase in CAT activity was observed when the RAR-β expression vector RAR-β0 was co-transfected with the vit-tk-CAT reporter gene instead of RAR-β-ER.CAS (data not shown).

To demonstrate directly that RAR-β binds RA, cytoplasmic extracts prepared from COS-1 cells transfected with the RAR-β0 expression vector were incubated with labelled RA in the presence or absence of excess unlabelled RA or retinol, as described for RAR-α by Petkovich et al. (1987). An increase in the specific, high affinity binding of RA was observed in the transfected cell extracts. As for RAR-α, Petkovich et al. (1987), however, there was high background binding in extracts of untransfected cells due to endogenous cellular retinoic acid binding protein (CRABP), thus precluding any accurate determination of the affinity of RA for its receptors (data not shown). The relative affinity of RA for RAR-α and RAR-β, was therefore, estimated by measuring the activation of vit-tk-CAT expression as a function of the ligand concentration under conditions where the reporter gene was present in large excess over the chimaeric receptor (30 ng of RAR-α-ER.CAS or RAR-β-ER.CAS per transfection, see FIG. 10(a) and FIG. 10(c), left panel). Under these conditions, the concentration of ligand leading to 50% of the maximum inducible CAT activity (ED$_{50}$) should reflect the relative affinity of the two chimaeric receptors for RA. In agreement with the previous report of Petkovich et al. (1987), the ED$_{50}$ for the RAR-α chimaera was close to $10^{-8}$M (FIGS. 10(b) and 10(c), right panel). In contrast, efficiency of RA in stimulating CAT activity was consistently ~10-fold greater with the RAR-β chimaera (ED$_{50}$ ~ $10^{-9}$M), suggesting that RAR-β has a 10-fold greater affinity for RA than RAR-α does. Note that for both RAR-α and RAR-β chimaeras, retinol was ~1,000-fold less efficient than RA at stimulating expression of the reporter gene. As previously discussed for RAR-α, however, it cannot be concluded that retinol is directly able to induce trans-activation by RAR-β, as it is known that retinol can be converted to RA in cultured cells, Williams et al. (1985).

The present data, together with previous studies, de The et al. (1987) and Petkovich et al. (1987), clearly establish the existence of two structurally closely-related human retinoic acid receptors encoded in two distinct genes which map to different chromosomes. The gene encoding the previously characterized retinoic acid receptor, Petkovich et al. (1987) and Giguere et al. (1987), designated here as RAR-α, maps to chromosome 17q21.1, Petkovich et al. and Matter et al., whereas the receptor RAR-β, also called hap, is encoded in a gene that maps to chromosome 3p24 (Mattei, M. G., H. d. T., A. M., P. T. and A. D., manuscript submitted). It is interesting that RAR-α and RAR-β are more homologous to the two closely-related thyroid hormone receptors TRα and TRβ, located on chromosomes 17q11.2, Petkovich et al. (1987) and Matter et al., and 3p21-25, Thompson et al. (1987) and Gareau et al. (1988), respectively, than to any other members of the nuclear receptor family, de The et al. (1987), Petkovich et al. (1987), and Giguere et al. (1987). These observations suggest that the thyroid hormone and retinoic acid receptors have evolved by gene, and possibly chromosome, duplications from a common ancestor, which itself diverged rather early in evolution from the common ancestor of the steroid receptor group of the family. In this respect, the counterparts of the human RAR-α and RAR-β genes are present in both mouse and chicken genomes (unpublished results).

Multiple effects of retinoids on both animal development and homeostasis have been reported, Petkovich et al. (1987), Giguere et al. (1987), Robertson (1987), and Sporn et al. (1984). Important clues to the mechanisms through which retinoids control many developmental and homeostatic processes will be obtained by determining the spatial and temporal patterns of expression of the various elements of the retinoid signal transduction system, including both the α and β receptors and the cellular retinoic acid and retinol binding proteins (CRABP and CRBP, Petkovich et al. (1987), Giguere et al. (1987), and Sporn et al. (1984). The high degree of homology between the putative DNA-binding domains (region C, 97% amino-acid identity) of RAR-α and RAR-β suggests that the two receptors might recognize a common RA-responsive element. Their difference in the A/B region, however, may result in differential gene activation, as the corresponding region of the human oestrogen receptor appears to play a specific role in the activation of different oestrogen-responsive genes, Kumar et al. (1987).

The results obtained in this invention indicate that RAR-β may mediate activation of transcription by RA at concentrations 10-fold lower than those necessary for activation by RAR-α, although both receptors respond to RA concentrations within the range observed for RA action in vivo. As the $ED_{50}$ values for the various biological effects of RA in cell culture span a wide range of concentrations ($4 \times 10^{-10}$ to greater than $10^{-8}$M, Sporn et al. (1984) at pp. 234–279, it is possible that the two RA receptors may be differentially involved in these effects.

C. Differential Expression and Ligand Regulation of the Retinoic Acid Receptor α and β Genes The recent cDNA cloning of several nuclear hormone receptors, including the steriod and thyroid hormone receptors, has revealed that their overall structures were strikingly similar. In particular, two highly conserved regions have been shown to correspond to the DNA- and hormone-binding domains (for review see Evans, 1988).

Analysis of a hepatitis B virus integration site in a human hepatocellular carcinoma led to the identification of a putative genomic exon highly homologous to the DNA-binding domain of other members of this nuclear receptor multigene family (Dejean et al., 1986). Two different cDNAs homologous to this sequence have recently been cloned (Giguere et al., 1987; Petkovich et al., 1987; de Thé et al., 1987) and their translation products identified as retinoic acid receptors (designated RAR α and RAR β) (Giguere et al., 1987; Petkovich et al., 1987; Brand et al., 1988). The two receptors have almost identical DNA- and hormone-binding domains but differ in their N-terminal part. Their respective genes map to different chromosomes, 17q21.1 for RAR α (Mattei et al., 1988) and 3p24 for RAR β (Mattei et al., 1988), and their nucleotide sequences are only distantly related. Both genes are found in most species (Brand et al., 1988 and de Thé, unpublished results), suggesting an early gene duplication. Analysis of the RA-dependent gene transactivation also showed that the ED 50 of RAR α and β were significantly different ($10^{-8}$ and $10^{-9}$M, respectively), indicating that RAR-β may mediate activation of transcription at RA concentrations 10-fold lower than those necessary for activation by RAR α (Brand et al., 1988).

The existence of two different retinoic acid receptors raises a number of questions as to the biological consequences of the RAR gene duplication. In particular, differences in the mechanisms of regulation or spatial expression patterns of the two receptors could account for distinct physiological roles. The tissue distribution of the transcripts for RAR α and β and their response to RA have been studied. The results show clear differences in the spatial patterns of expression and indicate that the β, but not the α, RAR gene is transcriptionally upregulated by RA in a protein synthesis-independent fashion. The discovery of differential expression of the RAR α and β genes, coupled with a selective regulation of RAR β gene expression by RA, may prove to be important components of retinoic acid physiology. These findings strongly suggest that the two receptors are differentially involved in the various biological effects of RA. The results obtained in the study are summarized below.

The RAR α gene, which is transcribed as two mRNA species of 3.2 and 2.3 kb, is overexpressed in the haematopoietic cell-lines and has an otherwise low level expression in all the other human tissues examined. By contrast, the RAR β gene exhibits a much more varied expression pattern. Indeed, the two transcripts, 3 and 2.5 kb, show large variations in their levels of expression which range from undetectable (haematopoietic cell-lines) to relatively abundant (kidney, cerebral cortex, etc.). Run-on studies with the hepatoma cell-lines show that, at least in some tissues, these differences may be due to an increase in the transcription rate of the RAR β gene. These findings point to complex regulatory mechanisms of RAR gene expression that may confer the cells with various sensitivities to RA.

The availability of cloned RAR cDNAs prompted an investigation of possible regulation of these receptor mRNAs by RA. Exposure of hepatoma cells to RA led to a rapid increase in the level of RAR β transcripts, while the abundance of RAR α transcriptions remained unaffected. The stimulation of expression of RAR β mRNAs was induced by physiological concentrations of RA in a dose-dependent manner. Such autoregulation is a general feature of hormonal systems and has been shown to take place at the mRNA and protein levels, in the case of the nuclear receptors for glucocorticoids (down-regulation, Okrent et al., 1986) or vitamin D3 (up-regulation, McDonnell et al., 1987). The RA-induced upregulation of the RAR β transcripts was observed in the presence of protein synthesis inhibitors. In vitro nuclear transcript run-on assays show that the RA-induced increase in RAR β mRNAs levels is the consequence of an enhanced transcription. These findings demonstrate that the RAR β gene is transcriptionally upregulated by the RA and provide the first identification of a primary target gene for RA. The cloning of the promoter sequences of the RAR β gene should allow the identification of the upstream genomic elements implicated in RA responsiveness. The use of these sequences will provide a useful tool to determine which one of the α and/or the β receptor is involved in regulating β RAR gene expression.

The haematopoietic cell-line HL60 has been widely used as a model for RA-induced differentiation (Strickland and Mahdavi, 1978). The data from this invention suggest that in this system RAR α must be responsible for the RA-induced differentiated phenotype, since HL60 does not appear to have any RAR β mRNAs. Note in this respect that Davies et al. (1985) studying the RA-dependent transglutaminase expression in these cells have found an ED 50 of $5 \times 10^{-8}$M consistent with a RAR α-mediated transactivation.

The upregulation of the β receptor gene by RA may have very important implications in developmental biology. Morphogen gradients are frequently implicated in cell commitment (Slack, 1987). One example of this phenomenon is the polarization of the chick limb bud where RA, the suspected morphogen, forms a concentration gradient across the anterior-posterior axis of the developing bud (Thaller and Eichele, 1987). However, the small magnitude of this gradient (2.5 fold) is puzzling and suggests the existence of amplification mechanisms (Robertson, 1987). Since transactivation of target genes is dependent upon both receptor and ligand concentrations, a small increase in RA may result in a disproportionately larger RAR β effect. The effect of this RA gradient could be potentiated by a corresponding gradient in RAR β receptors as a consequence of upregulation by RA itself.

C.1. Tissue distribution of the α and β RAR mRNAs

To study the differential expression of the RAR α and β genes, Northern blot analysis was performed using 5 μg (microgram) of poly(A)+RNA extracted from various human tissues and cell-lines. A RAR β clone previously identified (de Thé et al., 1987) was used to isolate a partial cDNA clone for RAR α from a hepatoma cell-line cDNA library, and the two cDNA inserts were used as probes. More particularly, poly-(A)+mRNA (5 μg) from different human tissues and cell-lines was denatured by glyoxal, separated on a 1.2% agarose gel, blotted onto nylon filters and hybridized to an α (FIG. 11, upper panel), then a β (FIG. 11, middle panel) RAR cDNA single-stranded probe (see materials and methods, infra). Exposure time was 36 h. The filters were subsequently hybridized to a β actin probe (FIG. 11, lower panel) to ensure that equal amounts of RNA were present in the different lanes. The following abbreviations are used in FIG. 11. Sp. cord: spinal cord. C. cortex: cerebral cortex. K562 and HL60 are two haematopoietic cell-lines. PLC/PRF/5 is a hepatoma derived cell-line.

Referring to FIG. 11, the spatial distribution patterns were clearly distinct between the two receptors. The RAR α probe hybridized to two transcripts of 3.2 and 2.3 kilobases (kb) with an approximately equal intensity. The two mRNAs were present at low levels in all tissues examined but were overexpressed in the haematopoietic cell-lines, K562 and HL60.

When the same filters were hybridized with the RAR β probe, a much more variable transcription pattern was observed (FIG. 11). Two mRNA species of 3 kb and 2.5 kb were visible in most tissues, except in the spinal cord and the liver (adult or fetal) where the smaller transcript was undetectable. Major quantitative differences in the level of expression of the two transcripts were noted. The tissues examined could be classified into four groups with respect to expression of β receptor mRNAs: high (kidney, prostate, spinal cord, cerebral cortex, PLC/PRF/5 cells), average (liver, spleen, uterus, ovary), low (breast, testis) and undetectable (K562 and HL60 cells). The use of a β probe that did not hybridize to α, allowed us to correct our previous description of β RAR transcripts in these haematopoietic cell-lines (de Thé et al., 1987). The suppression of β receptor gene expression, associated with an overexpression of RAR α mRNAs seems to be a general feature of haematopoietic cell-lines, since similar results were obtained when we repeated the study using six other cell-lines (HEL, LAMA, U937, KG1, CCRF, Burkitt) (data not shown).

C.2. RA-induced mRNA regulation

To investigate whether retinoic acid modulates the expression of its own receptor, PLC/PRF/5 cells were grown in the presence of various concentrations of RA for different times, and RAR α and β mRNAs were analysed by Northern blot hybridization. More particularly, semi-confluent cells were grown for 6 hr in charcoal stripped medium and retinoic acid was then added to the medium at various concentrations ($10^{-10}$M to $10^{-6}$M) for 4 hr. Control cells were treated with ethanol (E). Northern-blotting was performed as described in connection with FIG. 11, except that 30 μg of total RNA was used. Dose-response is shown in FIG. 10A.

Another analysis was performed as in FIG. 12A, except that $10^{-6}$M RA was used for various times (0–12 h). Time-response is shown in FIG. 12B. Exposure time was 12 hr for the β probe (FIG. 10B, lower panel) and four days for the α probe (FIG. 12B, upper panel).

When the cells were treated with a high concentration of RA ($10^{-6}$M), a rapid increase in β receptor mRNAs was observed, an a dose-response analysis showed that this stimulatory effect was already evident at a RA concentration of $10^{-9}$M (FIG. 12A, lower panel). From densitometry, the magnitude of the RA-induced upregulation was 10-fold.

Since the PLC/PRF/5 cells constitutively overexpress the RAR β mRNAs (FIG. 11), the experiment was repeated using the HEPG2 hepatoma cell-line, which has a level of RAR β expression similar to that of normal adult liver (de Thé et al., 1987). In this case, there was a greater (50-fold) RA-induced stimulation of the levels of RAR β mRNAs (data not shown). Exposure of the PLC/PRF/5 cells to RA ($10^{-6}$M) during various periods indicated that the induction has a latency of one hour, was complete after four hours, and did not decrease after an overnight treatment (FIG. 12B, lower panel). After hybridizing the same filters with an RAR α probe, no variation was found in the level of the α receptor mRNAs (FIG. 12, upper panel), indicating that RA had no effect on the expression of the RAR α gene.

C.3. Effect of inhibitors

To investigate the mechanism of activation of RAR β gene by RA, experiments with PLC/PRF/5 cells were performed in the presence or absence of various inhibitors of transcription or translation, or were treated with ethanol (E) as a control.

More particularly, PLC/PRF/5 cells were exposed to charcoal stripped medium for 6 hr; subsequently ethanol (E), RA ($10^{-6}$M) and/or inhibitors cycloheximide (CH) 10 μg/ml or actinomycin D (AC) (5 μg/ml) were added for an additional 4 hr. Northern-blotting was carried on using 30 μg of total RNA. FIG. 13 shows filters hybridized first to the RAR β probe (FIG. 13, right panel), then to the α probe (FIG. 13, left panel), and finally to a β actin probe (FIG. 13, lower panel). Exposure times were the same as for the experiments in FIG. 12.

The RNA synthesis inhibitor actinomycin D (AC) abolished the RA-induced increase in the levels of RAR β transcripts (compare the RA+AC lane to the RA and E+AC lanes), while the protein synthesis inhibitor cycloheximide (CH) did not (compare lanes RA+CH to CH). Neither RA, AC, nor CH significantly affected the levels of β actin mRNA (FIG. 13, lower panel). These findings suggest that RA-induction of the β receptor gene results from a direct transcriptional effect. When the same filters were rehybridized to the RAR α probe (FIG. 13, left panel) the presence or absence of RA had no effect on the levels of RAR α mRNAs confirming that the RAR α gene is not regulated by RA.

C.4. Nuclear transcript elongation analysis

Nuclear run-on experiments were carried out to determine if the enhanced expression of the RAR β gene was due to increased transcription. PRF/PLC/5 cells were grown in the presence of ethanol (E) or retinoic acid (RA), their nuclei were isolated, and transcription was performed in the presence of ($^{32}$P)UTP. The labelled RNAs were hybridized to filters containing single-stranded RAR β cDNA inserts in the appropriate orientation (S (sense) 10 μg and 1 μg), or in the reverse orientation (AS (antisense) 20 μg). A β actin control was also included. Exposure time was 12 hours. The results are shown in FIG. 14.

The specific hybridization, which reflects the transcription rate, is clearly induced by RA. In addition, the magnitude of the increase in RAR β mRNAs is comparable when assessed by run-on assays (5 to 7 fold) or Northern analysis (8 to 10 fold). These experiments establish that the RAR β gene is transcriptionally upregulated by RA.

Nuclear transcript elongation assays were also used to investigate whether the higher steady-state levels of RAR β mRNAs observed in the hepatoma cells PRF/PLC/5 compared to HEPG 2 (de Thé et al., 1987), were related to differences in transcription rates. Transcript elongation assays were performed with PRF/PLC/5 and HEPG2 cells as described below in material and methods, in the absence of added RA. The filters contained, respectively, 10 μg and 20 μg of sense (S) and antisense (AS) RAR β cDNA inserts. Exposure time was 24 hours. The results are shown in FIG. 15.

A much greater specific hybridization signal, relative to the β actin control, was observed in PRF/PLC/5 cells compared to the HEPG 2 cells (FIG. 15), indicating that their transcription rates are different. This result suggests that at least some of the variations in RAR β expression in the human tissues and cell-lines (FIG. 11) might be due, in a similar manner, to differences in the transcription rates of the RAR β gene.

C.5. Stability of RAR mRNAs

The level of RAR β mRNAs was slightly higher after cycloheximide treatment (compare the E lane to the CH lane in FIG. 13, right panel). In the presence of RA, CH treatment caused approximately a 50-fold increase in the level of RAR β gene expression (compare lane E to RA+CH). Such superinduction by cycloheximide has been described for several genes and associated with either transcriptional or post-transcriptional mechanisms (Greenberg et al., 1986).

To determine whether RNA stabilization was involved in the induction by CH, PLC/PRF/5 cells were first stimulated for 3 hours by RA ($10^{-6}$M) in the presence of CH (10 μg/ml) and extensively masked with culture medium. Transcription was then blocked by addition of actinomycin D (5 μg/ml) and the level of RAR mRNAs was monitored for the next 5 hours in the presence or absence of CH. Northern-blotting was done using 30 μg of total RNA. The results are shown in FIG. 16. The filters were hybridized first to the RAR β probe (FIG. 16, right panel), then to the α probe (FIG. 16, left panel), and lastly to a β actin probe (FIG. 16, lower panel). Exposure times were as in FIG. 12.

Quantification of the RAR β mRNAs levels indicated that CH indeed stabilized the β transcripts, as CH increased their half-life from approximately 50 to 80 min (FIG. 16, right panel). The combined effect of increased transcription and reduced degradation may account for the synergistic effect of RA and CH on β mRNAs levels. In the case of RAR α, cycloheximide treatment caused only a slight increase in mRNAs levels and no superinduction by RA was observed (FIG. 13, left panel). In addition, the α receptor mRNAs, which have a half life of at least 5 hours, are more stable than the RAR β transcripts (FIG. 16, left panel). A pentanucleotide, ATTTA, in A/T rich 3' non-coding regions seems to mediate mRNA degradation (Shaw and Kamen, 1986). The 3.2 kb RAR α transcript has an A/T poor 3' end (38%) and contains two such motifs (Giguere et al., 1987; Petkovich et al., 1987), whereas the 3 kb RAR β mRNA has an A/T rich 3' end (68%) and four copies fo ATTTA (de Thé et al., 1987). These findings are consistent with the differences in RAR α and β mRNAs stability that have been observed.

C.6. Material and Methods

C.6.1. Biological samples and cell-lines.

Human tissue samples were obtained from early autopsies and kept at $-80°$ C. prior to extraction. The HEPG 2 and PLC/PRF/5 hepatoma cell-lines were grown in Dulbecco's modified Eagle's medium with 10% fetal calf serum, glutamine, and antibiotics, in 5% $CO_2$. Semiconfluent cells were treated with RA after a 6 h washout in charcoal stripped medium. All-trans-retinoic acid was obtained from Sigma. Cycloheximide and actinomycin D (both from Sigma) were used at concentrations of 10 and 5 μg/ml micrograms/milliliter), respectively.

C.6.2. RNA preparation.

The RNA was prepared by the hot phenol procedure (Maniatis et al., 1982). Poly(A)+ mRNA was prepared by oligo(dT)-cellulose chromatography. For Northern-blot analysis, total RNA (30 μg) or poly(A)+mRNA (5 μg) was denatured by glyoxal and fractionated on a 1.2% agarose gel (maniatis et al., 1982). The nucleic acid was transferred to nylon membranes (Amersham) by blotting and attached by UV exposure plus baking.

C.6.3. Recombinant clones.

The β receptor probe was a 600 bp fragment of the cDNA previously described (de Thé et al., 1987) extending from the 5' end to the Xho I site, corresponding to 5' untranslated region and the A/B domain. The α receptor probe was a short cDNA insert that was isolated from a PLC/PRF/5 human hepatoma cell-line cDNA library generated as described (Watson and Jackson, 1986). This library was hybridized with an RAR β-derived probe (nucleotides 550 to 760) corresponding to the conserved DNA-binding domain of RAR β. A weakly hybridizing plaque was purified, subcloned into M13mp18, and sequenced by the dideoxy procedure. This clone was found to be identical to RAR α and extended from nucleotides 358 to 587, corresponding to the C and D domains (Giguere et al., 1987). Since this cDNA insert contains some regions homologous to the RAR β cDNA, cross-hybridization has been occasionally observed, particularly in cell-lines that overexpress RAR β mRNAs.

C.6.4. Hybridization procedure.

The two cDNA inserts were subcloned into M13 and used to generate high specific activity (greater than $10^9$ c.p.m./μg) single-stranded probes by elongation of a sequencing primer with $^{32}P$ labelled dTTP (3000 Ci/mmol) and unlabelled nucleotides by Klenow polymerase. The resulting double-stranded DNA was digested using a unique site in the vector, fractioned on a urea/acrylamide sequencing gel, and the labelled single-stranded insert electroeluted. These probes ($5 \times 10^6$ cpm/ml) were hybridized to the filters in 7% (w/v) sodium dodecyl sulfate (SDS), 0.5M $NaPO_4$ pH 6.5, 1 mM ethylenediaminetetraacetate (EDTA), and 1 mg/ml bovine serum albumin (BSA) at 68° C. overnight. The filters were washed in 1% SDS, 50 mM NaCl, 1 mM EDTA at 68° C. for 10 min and autoradiographed at $-70°$ C. using Kodak XAR films and intensifying screens. A mouse β actin probe was used to rehybridize the filters and check that all lanes contained equal amounts of RNA.

C.6.5. Nuclear run-on experiments.

Nuclear transcript elongation assays were performed as described (Mezger et al., 1987). PLC/PRF/5 or HEPG 2 cells ($10^8$) were challenged with ethanol or with $10^{-6}M$ RA for 6 hours in charcoal-stripped medium. After isolation of the nuclei, transcription was performed in a final volume of 100 μl (microliters) with 150 μCi (microcuries) of ($α^{32}P$) UTP (3000 Ci/mmol). Typical incorporation ranged between 2 and $6 \times 10^7$ cpm. The labelled RNA was hybridized to nylon filters (Amersham) containing 10 μg and 1 μg of a 3' end RAR β cDNA insert (position 2495 to 2992, de Thé et al., 1987) cloned in M13; 20 μg of the same insert in the reverse orientation were included as a negative control. A plasmid containing a mouse β actin insert (4 μg) provided a positive and quantitative hybridization control. Hybridization was performed with a probe concentration of $2-6 \times 10^7$ cpm/ml for 48 hours.

The relative intensity of hybridization signals in Northern-blotting and run-on experiments was estimated using a Hoefer scanning densitometer and the appropriate computer program.

Our results showing a direct autoregulation of the transcription of the RAR-β gene implies that the retinoic acid receptor β binds to its own gene promotor sequences. To identify those sequences, several 5' coterminal RAR-β cDNA clones were derived from the PRF/PLC/5 library previously described. Nucleotide sequence analysis showed that these clones extended our previous λ 13 RAR-β clone by 72 bp, which are shown in FIG. 17. Thus, this invention also provides the 72 bp nucleotide sequence shown in FIG. 17, as well as a cloned DNA sequence encoding a polypeptide of hap gene, wherein the sequence has the formula

```
                                                                CCCATGC
GACCTGTTTGAAGGACTGGGATGCCGAGAACGCGAGCGATCCGAGCAGGGTTTGTCTGGGCACCGT
ATGTTTGACTGTATGGATGTTCTGTCAGTGAGTCCTGGGCAAATCCTGATTCTACACTGCGAGTCC
GTCTTCCTGCATGCTCCAGGAGAAAGCTCTCAAAGCATGCTTCAGTGGATTGACCCAAACCGAATG
GCAGCATCGGCACACTGCTCAATCAATTGAAACACAGAGCACCAGCTCTGAGGAACTCGTCCCAAG
CCCCCCATCTCCACTTCCTCCCCCTCGAGTGATCAAACCCTGCTTCGTCTGCCAGGACAAATCATC
AGGGTACCACTATGGGGTCAGCGCCTGTGAGGGATGAAGGGCTTTTTCCGCAGAAGTATTCAGAAG
AATATGATTTACACTTGTCACCGAGATAAGAACTGTGTTATTAATAAAGTCACCAGGAATCGATGC
CAATACTGTCGACTCCAGAAGTGCTTTGAAGTGGGAATGTCCAAAGAATCTGTCAGGAATGACAGG
AACAAGAAAAGAAGGAGACTTCGAAGCAAGAATGCACAGAGAGCTATGAAATGACAGCTGAGTTG
GACGATCTCACAGAGAAGATCCGAAAAGCTCACCAGGAAACTTTCCCTTCACTCTCGCAGCTGGGT
AAATACACCACGAATTCCAGTGCTGACCATCGAGTCCGACTGGACCTGGGCCTCTGGGACAAATTC
```

-continued

```
AGTGAACTGGCCACCAAGTGCATTATTAAGATCGTGGAGTTTGCTAAACGTCTGCCTGGTTTCACT

GGCTTGACCATCGCAGACCAAATTACCCTGCTGAAGGCCGCCTGCCTGGACATCCTGATTCTTAGA

ATTTGCACCAGGTATACCCCAGAACAAGACACCATGACTTTCTCAGACGGCCTTACCCTAAATCGA

ACTCAGATGCACAATGCTGGATTTGGTCCTCTGACTGACCTTGTGTTCACCTTTGCCAACCAGCTC

CTGCCTTTGGAAATGGATGACACAGAAACAGGCCTTCTCAGTGCCATCTGCTTAATCTGTGGAGAC

CGCCAGGACCTTGAGGAACCGACAAAAGTAGATAAGCTACAAGAACCATTGCTGGAAGCACTAAAA

ATTTATATCAGAAAAAGACGACCCAGCAAGCCTCACATGTTTCCAAAGATCTTAATGAAAATCACA

GATCTCCGTAGCATCAGTGCTAAAGGTGCAGAGCGTGTAATTACCTTGAAAATGGAAATTCCTGGA

TCAATGCCACCTCTCATTCAAGAAATGATGGAGAATTCTGAAGGACATGAACCCTTGACCCCAAGT

TCAAGTGGGAACACAGCAGAGCACAGTCCTAGCATCTCACCCAGCTCAGTGGAAAACAGTGGGGTC

AGTCAGTCACCACTCGTGCAATAA,
``` and serotypic variants thereof, wherein said DNA is in a purified form.

This 72 bp sequence was used as a probe to screen a human genomic library. Six overlapping clones were derived, and a 6 kb HindIII-BamHI insert containing the probe was subcloned into PTZ 18 at the same sites to give rise to the plasmid pPROHAP. Since this genomic DNA insert is limited by the BamHI site present in the original λ13 clone and contains the additional 72 bp of the 5' end of the mRNA, it also contains the promotor region and all the elements necessary for the RAR-β gene expression and regulation. S1 analysis using the plasmid pPROHAP end labelled at the BamHI site suggest that the cloned RAR-β cDNA is not full-size and that the cap site is indeed located in the 129 bp SmaI-EcoRI fragment, 70 bp upstream from the EcoRI site.

A complete restriction map of the HindIII-BamHI genomic DNA insert is shown in FIG. 18.

Plasmid pPROHAP was transfected into the E. coli strain DH5αF' (from B.R.L.). A viable culture of E. coli strain DH5αF' transformed with plasmid pPROHAP was deposited on Nov. 29, 1988, with the National Collection of Cultures of Microorganisms or Collection Nationale de Cultures de Micro-organisms (C.N.C.M.) of Institut Pasteur, Paris, France, under Culture Collection Accession No. C.N.C.M. I-821.

This DNA insert, which is characterized by its restriction map and partial nucleotide sequence (or some of its fragment), provides a tool to assess RAR-β function, because it must contain a RARE (Retinoic Acid Responsive Enhancer). Several constructs in which this promotor region controls the expression of indicator genes, such as the β-galactosidase or the chloramphenicol acetyl transferase (CAT), have been designed. Transient or stable expression, in eucaryotic cells, of these constructs, together with an expression vector of RAR-β or RAR-α, provides a useful model system to directly assess stimulation of RAR-β by a retinoid.

Thus, this invention also provides a recombinant DNA molecule comprising a DNA sequence coding for a retinoic acid receptor, said DNA sequence coding for expression in a unicellular host or eukaryotic cells or yeasts of a polypeptide which is the retinoic acid receptor. This invention also provides a recombinant DNA molecule comprising the promoter region of the RAR-β gene.

It should be apparent that the foregoing techniques as well as other techniques known in the field of medicinal chemistry can be employed to assay for agonists and antagonists of ligand binding to RAR-β and binding of the RAR-β protein to DNA. Specifically, this invention makes it possible to assay for a substance that enhances the interaction of the ligand, the RAR-β protein, the DNA, or combinations of these materials to elicit an observable or measurable response. The substance can be an endogenous physiological substance or it can be a natural or synthetic drug.

This invention also makes it possible to assay for an antagonist that inhibits the effect of an agonist, but has no biological activity of its own in the RAR-β effector system. Thus, for example, the invention can be employed to assay for a natural or synthetic substance that competes for the same receptor site on the RAR-β protein or the DNA that the agonist occupies, or the invention can be employed to assay for a substance that can act on an allosteric site, which may result in allosteric inhibition.

It will be understood that this invention is not limited to assaying for substances that interact only in a particular way, but rather the invention is applicable to assaying for natural or synthetic substances, which can act on one or more of the receptor or recognition sites, including agonist binding sites, competitive antagonist binding sites (accessory sites), and non-competitive antagonist or regulatory binding sites (allosteric sites).

A convenient procedure for carrying out the method of the invention involves assaying a system for stimulation of RAR-β by a retinoid. For instance, as a retinoid binds to the receptor, the receptor-ligand complex will bind to the responsive promotor sequences and will activate transcription. For example, transcription of the β-galactosidase or CAT genes can be determined. The method of this invention makes it possible to screen β-receptor binding retinoids. In addition, this invention makes it possible to carry out blood tests for RAR-β activity in patients.

In summary, a hepatitis B virus (HBV) integration in a 147 bp cellular DNA fragment homologous to steroid receptors and c-erbA/thyroid hormone receptor genes previously isolated from a human hepatocellular carcinoma (HCC) was used as a probe to clone the corresponding complementary DNA from a human liver cDNA library. The nucleotide sequence analysis revealed that the overall structure of the cellular gene, named hap, is similar to that of DNA-binding hormone receptors. That is, it displays two highly conserved regions identified as the putative DNA-binding and hormone-binding domains of the c-erbA/steroid receptors. Six out of seven hepatoma and hepatoma-derived cell-lines express a 2.5 kb hap mRNA species which is undetectable in normal adult and fetal livers but present in all non-hepatic tissues analyzed. Low stringency hybridization experiments revealed the existence of hap related genes in the human genome. Taken together, the data suggest that the hap product may be a member of a new family of ligand-responsive regulatory proteins whose inappropriate expression in liver seems to correlate with the hepatocellular transformed state.

Because the known receptors control the expression of target genes that are crucial for cellular growth and differentiation, an altered receptor could participate in the cell transformation. In that sense, avian v-erbA oncogene, which does not by itself induce neoplasms in animals, potentiates the erythroblast transformant effects of v-erbB and other oncogenes of the src family (Kahn et al., 1986). It has been shown that the v-erbA protein has lost its hormone-binding potential (Sap et al., 1986), presumably as a result of one or several mutations it has accumulated in its putative ligand-binding domain. It has been also suggested (Edwards et al., 1979) that the growth of human breast tumors are correlated to the presence of significant levels of ER. This invention may provide a novel example in which a DNA-binding protein would again relate to the oncogenic transformation by interfering with the transcriptional regulation of target genes. DNA-transfection assays using the native hap cDNA as well as 'altered' hap genes derived from various HCC can provide important information concerning any transforming capacity.

Following is a more detailed identification of the literature citations appearing above:

Beasley, R. P., and Hwang, L. Y. (1984). Epidemiology of Hepatocellular Carcinoma In Viral Hepatitis and Liver Disease, G. N. Vyas, J. L. Dienstag, J. H. Hoofnagle, eds, (Grune and Stratton, Inc.), pp. 209-224.

Berg, J. M. (1986). More metal-binding fingers. Nature, 319, 264-265.

Biggin, M. D., Gibson, T. J. and Hong, G. F. (1983). Buffer gradient gels and $^{35}$S label as an aid to rapid DNA sequence determination. Proc. Natl. Acad. Sci. USA, 80, 3963-3965.

Brand, N., Petkovich, M., Krust, A., Chambon, P., de Thé, H., Marchio, A., Tiollais P., and Dejean, A. (1988) Nature 332, 850-853.

Bréchot, C., Pourcel, C., Louise, A., Rain, B. and Tiollais, P. (1980). Presence of integrated hepatitis B virus DNA sequences in cellular DNA of human hepatocellular carcinoma. Nature, 286, 533-535.

Breitman, T. R., Selonick, S. E. and Collins, S. J. (1980) Proc: Natl. Acad. Sci. USA 77, 2936-2940.

Chakraborty, P. R., Ruiz-Opazo, N., Shouval, D. and Shafritz, D. A. (1980). Nature, 286, 531-533.

Chen, D. S., Hoyer, B. H., Nelson, J., Purcell, R. H. and Gerin, J. L. (1982). Detection and properties of hepatitis B viral DNA in liver tissues from patients with hepatocellular carcinoma. Hepatology, 2, 42S-45S.

Chytil, F. J. and Ong, D. E. (1984) in The retinoids Vol. 2, eds. Sporn, M. B., Roberts, A. B. and Goodman, D. S. (Academic Press, New York) pp. 89-123.

Conneely, O. M., Sullivan, W. P., Toft, D. O., Birnbaumer, M., Cook, R. G., Maxwell, B. L., Zarucid-Schulz, T., Greene, G. L., Schrader, W. T. and O'Malley, B. W. (1986). Molecular cloning of the chicken progesterone receptor. Science, 233, 767-770.

Davies, P. J., Murtaugh, M. P., Moore, W. T., Johnson, G. S. and Lucas, D. (1985) J. Biol. Chem. 260, 5166-5174.

Dejean, A., Bougueleret, L., Grzeschik, K. H. and Tiollais, P. (1986). Hepatitis B virus DNA integration in a sequence homologous to v-erbA and steroid receptor genes in a hepatocellular carcinoma. Nature, 322, 70-72.

Diakun, G. P., Fairall, L. and Klug, A. (1986). EXAFS study of the zinc-binding sites in the protein transcription factor IIIA. Nature, 324, 698-699.

Edman, J. C., Gray, P., Valenzuela, P., Rall, L. B. and Rutter, W. J. (1980). Integration of hepatitis B virus sequences and their expression in a human hepatoma cell. Nature, 286, 535-538.

Edwards, D. P., Chamness, G. C., McGuire, W. L. (1979). Estrogen and progesterone receptor proteins in breast cancer. Biochimica et Biophysica Acta, 560, 457-486.

Evans, R. M. (1988) Science 240, 899-895.

Gareau, J. L., Houle, B., Leduc, F., Bradley, W. E. C. & Dobrovic, A. Nucleic Acids Res. 16, 1223 (1988).

Giguere, V., Hollenberg, S. M., Rosenfeld, M. G. and Evans, R. M. (1986). Functional Domains of the human glucocorticoid receptor. Cell, 46, 645-652.

Giguere, V., Ong, E. S., Segui, P. and Evans, R. M. (1987) Nature 330, 624-629.

Green, S., Walter, P., Kumar, V., Krust, A., Bornert, J. M., Argos, P. and Chambon, P. (1986). Human oestrogen receptor cDNA: sequence, expression and homology to v-erb-A. Nature, 320, 134-139.

Green, S. and Chambon, P. (1986). A superfamily of potentially oncogenic hormone receptors. Nature, 324, 615-617. Green, S. & Chambon, P. Nature 325, 75-78 (1987).

Green, S., Issemann, I. & Scheer, E. Nucleic Acids Res. 16, 369 (1988).

Greenberg, M. E., Hermanowski, A. L. and Ziff, E. B. (1986) Mol. Cell. Biol. 6, 1050-1057.

Greene, G. L., Gilna, P., Waterfield, M., Baker, A., Hort, Y. and Shine, J. (1986). Sequence and expression of human estrogen receptor complementary DNA, Science, 231, 1150-1154.

Gubler, U. and Hoffman, B. J. (1983). A simple and very efficient method for generating cDNA libraries. Gene, 25, 263-269.

Hanahan, D. (1983). Studies on transformation of *Escherichia coli* with plasmids. J. Mol. Biol. 166, 557-580.

Hollenberg, S. M., Weinberger, C., Ong., E. S., Cerelli, G., Oro, A., Lebo, R., Thompson, E. G., Rosenfeld, M. G. and Evans, R. M. (1985). Primary structure and expression of a functional human glucocorticoid receptor. Cell, 49, 39-46.

Jansson, M., Philipson, L. and Vennstrom, B. (1983). Isolation and characterization of multiple human genes homologous to the oncogenes of avian erythroblastosis virus. The EMBO J., 2, 561-565.

Kahn, P., Frykberg, L., Brady, C., Stanley, I., Beug, H., Vennstrom, B. and Graf, T. (1986). v-erbA cooperates with sarcoma oncogenes in leukemic cell transformation. Cell, 45, 349-356.

Kozak, M., (1986). Bifunctional messenger RNAs in eukaryotes. Cell, 47, 481-483.

Krust, A., Green, S., Argos, P., Kumar, V., Walter, P., Bornert, J. M. and Chambon, P. (1986). The chicken oestrogen receptor sequence: homology with v-erbA and the human oestrogen and glucocorticoid receptors. The EMBO J., 5, 891–897.

Kumar, V., Green, S., Staub, A. and Chambon, P. (1986). Localisation of the oestradiol-binding and putative DNA-binding domains of the human oestrogen receptor. The EMBO J., 5, 2231–2236.

Kumar, V. et al. Cell 51, 941–951 (1987).

Loosfelt, H., Atger, M., Misrahi, M., Guiochon-Mantel, A., Meriel, C., Logeat, F., Bernarous, R. and Milgrom, E. (1986). Cloning and sequence analysis of rabbit progesterone-receptor complementary DNA. Proc. Natl. Acad. Sci. USA, 83, 9045–9049.

Maniatis, T., Fritch, E. and Sambrook, J. (1982). Molecular cloning: a laboratory manual (Cold Spring Harbor, New-York: Cold Spring Harbor Laboratory).

McDonnell, D. P., Mangelsdorf, D. J., Pike, J. W., Haussler, M. R. and O'Malley, B. W. (1987). Molecular cloning of complementary DNA encoding the avian receptor for vitamin D. Science, 235, 1214–1217.

Mattei, M. G., Petkovich, M., Mattei, J. F., Brand, N. and Chambon, P., Hum. Genet. Mapping of the human retinoic acid receptor to q21 bend of chromosome 17. 1988, 80, 186–188.

Mattei, M. G., de Thé, H., Mattei, J. F., Marchio, A., Tiollais, P. and Dejean A., Assignment of the human hap retinoic acid receptor RAR-β gene to the p24 pend of chromosome 3, Hum. Genet. 1988, 80, 189–190.

McDonnell, D. P., Mangelsdorf, D. J., Pike, J. W., Haussler, M. R. and O'Malley, B. M. (1987) Science 235, 1214–1217.

Mezger, V., Bensaude, O., and Morange, M. (1987) Dev. Biol. 124, 544–550.

Miesfeld, R., Rusconi, S., Godowski, P. J., Maler, B. A., Okret, S., Wilkstrom, A. C., Gustafsson, J. A. and Yamamoto, K. R. (1986). Genetic complementation of a glucocorticoid receptor deficiency by expression of cloned receptor cDNA. Cell, 46, 389–399.

Miesfeld, R., Godowski, P. J., Maler, B. A. and Yamamoto, K. R. (1987). Glucocorticoid receptor mutants that define a small region sufficient for enhancer activation. Science, 236, 423–427.

Miller, J., McLachlan, A. D. and Klug, A. (1985). Repetitive zinc-binding domains in the protein transcription factor IIIA from Xenopus oocytes. The EMBO J., 4, 1609–1614.

Nguyen Van Cong, Weil, D., Finaz, C., Cohen-Haguenauer, O., Gross, M. S., Jegou-Foubert, C., de Tand, M. F., Cochet, C., de Grouchy, J., Frezal, J. (1986). Panel of twenty-five independent man-rodent hybrids for human genetic marker mapping. Ann. Genet., 29, 20–26.

Okrent, S., Poellinger, L., Dong, Y., and Gustafsson, J. A. (1986) Proc. Natl. Acad. Sci. USA 83, 5899–5903.

Petkovich, M., Brand, N. J., Krust, A. and Chambon, P. (1987) Nature 330, 444–450.

Roberts, A. B. and Sporn, M. B. (1984) in The retinoids Vol. 2, eds.

Robertson, M. (1987) Nature 330, 420–421.

Rosenberg, U. G., Schroder, C., Preiss, A., Kienlin, A., Coté, S., Riede, I. and Jackle, H. (1986). Structural homology of the product of the Drosophila Kruppel gene with Xenopus transcription factor IIIA. Nature, 319, 336–339.

Rusconi, S. & Yamamoto, K. R. Embo J. 6, 1309–1315 (1987).

Sanger, F., Nicklen, S. and Coulson, A. R. (1977). DNA sequencing with chain-terminating inhibitors. Proc. Natl. Acad. Sci. USA, 74, 5463–5467.

Sap, J., Munoz, A., Damm, K., Goldberg, Y., Ghysdael, J., Leutz, A., Beug, H. and Vennstrom, B. (1986). The c-erb-A protein is a high affinity receptor for thyroid hormone. Nature, 324, 635–640.

Shaw, G. and Kamen, R. (1986) Cell 46, 659–667.

Slack, J. M. W. (1987) Nature 327, 553–554.

Sporn, M. B., Roberts, A. B. and Goodman, D. S. (eds.), The Retinoid (Academic Press, New York) pp. 209–286.

Sporn, M. B. & Roberts, A. B. in The Retinoids Vol. 1 (eds Sporn, M. B., Roberts, A. B. & Goodman, D. S.) 235–279 (Academic Press, Florida, 1984).

Strickland, S. and Mahdavi, M. (1978) Cell 15, 393–403.

Szmuness, W. (1973). Hepatocellular carcinoma and the hepatitis B virus evidence for a causal association. Prog. Med. Virol., 24, 40–69.

Thaller, C. and Eichele, G. (1987) Nature 327, 625–628.

de Thé, H., Marchio, A., Tiollais, P. and Dejean, A. (1987) Nature 330, 667–670.

Thompson, C. C., Weinberger, C., Lebo, R. & Evans, R. M. Science 237, 1610–1614 (1987).

Tiollais, P., Pourcel, C. and Dejean, A. (1985). The hepatitis B virus. Nature, 317, 489–495.

Watson, C. F. and Jackson, J. F. (1986) in DNA Cloning Techniques: A Practical Approach, ed. Glover, D. (IRL, Oxford), pp. 79–88.

Weinberger, C., Thompson, C. C., Ong, E. S., Lebo, R., Gruol, D. J. and Evans, R. M. (1986). The c-erb-A gene encodes a thyroid hormone receptor. Nature, 324, 641–646.

Wilbur, W. J. and Lipman, D. J. (1983). Rapid similarity searches of nucleic acid and protein data banks. Proc. Natl. Acad. Sci. USA, 80, 726–730.

Williams, J. B. & Napoli, J. L. Proc Natn. Acad. Sci. U.S.A. 82, 4658–4662 (1985).

Yamamoto, K. R. (1985). Steroid receptor regulated transcription of specific genes and gene networks. Ann. Rev. Genet., 19, 209–252.

What is claimed is:

1. A purified form of an antibody specific for a peptide of the retinoic acid receptor RAR-β having the amino acid sequence MetPheAspCysMetAspValLeuSerValSerProGlyGlnIle
LeuAspPheTyrThrAla SerProSerSerCysMetLeuGlnGluLysAlaLeuLysAlaCys
PheSerGlyLeuThrGln ThrGluTrpGlnHisArgHisThrAlaGlnSerIleGluThrGln
SerThrSerSerGluGlu LeuValProSerProProSerProLeuProProProArgValTyr
LysProCysPheValCys GlnAspLysSerSerGlyTyrHisTyrGlyValSerAlaCysGlu
GlyCysLysGlyPhePhe ArgArgSerIleGlnLysAsnMetIleTyrThrCysHisArgAsp
LysAsnCysValIleAsn LysValThrArgAsnArgCysGlnTyrCysArgLeuGlnLysCys
PheGluValGlyMetSer LysGluSerValArgAsnAspArgAsnLysLysLysLysGluThr
SerLysGlnGluCysThr GluSerTyrGluMetThrAlaGluLeuAspAspLeuThrGluLys
IleArgLysAlaHisGln -continued GluThrPheProSerLeuCysGlnLeuGlyLysTyrThrThrAsn
SerSerAlaAspHisArg ValArgLeuAspLeuGlyLeuTrpAspLysPheSerGluLeuAla
ThrLysCysIleIleLys IleValGluPheAlaLysArgLeuProGlyPheThrGlyLeuThr
IleAlaAspGlnIleThr LeuLeuLysAlaAlaCysLeuAspIleLeuIleLeuArgIleCys
ThrArgTyrThrProGlu GlnAspThrMetThrPheSerAspGlyLeuThrLeuAsnArgThr
GlnMetHisAsnAlaGly PheGlyProLeuThrAspLeuValPheThrPheAlaAsnGlnLeu
LeuProLeuGluMetAsp AspThrGluThrGlyLeuLeuSerAlaIleCysLeuIleCysGly
AspArgGlnAspLeuGlu GluProThrLysValAspLysLeuGlnGluProLeuLeuGluAla
LeuLysIleTyrIleArg LysArgArgProSerLysProHisMetPheProLysIleLeuMet
LysIleThrAspLeuArg SerIleSerAlaLysGlyAlaGluArgValIleThrLeuLysMet GluIleProGlySerMet
ProProLeuIleGlnGluMetMetGluAsnSerGluGlyHisGlu
ProLeuThrProSerSer SerGlyAsnThrAlaGluHisSerProSerIleSerProSerSer
ValGluAsnSerGlyVal SerGlnSerProLeuValGln.

2. The antibody according to claim 1 which is specific for a peptide of the retinoic acid receptor RAR-β having the amino acid sequence GlnHisArgHisThrAlaGlnSerIleGluThrGlnSerThrSerSerGluGlu LeuValProSerProProSerProLeuProProProArgValTyrLysProCysPheValCys GlnAspLysSerSerGlyTyrHisTyrGlyValSerAlaCysGluGlyCysLysGlyPhePhe ArgArgSerIleGlnLysAsnMetIleTyrThrCysHisArgAspLysAsnCysValIleAsn LysValThrArgAsnArgCysGlnTyrCysArgLeuGlnLysCysPheGluValGlyMetSer LysGluSerValArgAsnAspArgAsnLysLysLysLysGluThrSerLysGlnGluCysThr GluSerTyrGluMetThrAlaGluLeuAspAspLeuThrGluLysIleArgLysAlaHisGln GluThrPheProSerLeuCys.

3. The antibody according to claim 1 which is specific for a peptide fragment of the retinoic acid receptor RAR-β having the amino acid sequence ValArgAsnAspArgAsnLysLysLysLysGluThrSerLysGlnGluCys.

4. The antibody according to claim 1 which is specific for a peptide fragment of the retinoic acid receptor RAR-β having the amino acid sequence AsnAspArgAsnLysLysLysLysGluThrCys.

5. The antibody according to claim 1 which is specific for a peptide fragment of the retinoic acid receptor RAR-β having the amino acid sequence CysGlyValSerGlnSerProLeuValGln.

6. The antibody according to claim 1 which is specific for a peptide fragment of the retinoic acid receptor RAR-β having the amino acid sequence AlaGluLeuAspAspLeuThrGluLysIleArg.

7. The antibody according to claim 1 which is specific for a peptide fragment of the retinoic acid receptor RAR-β having the amino acid sequence MetPheAspCysMetAspValLeuSerValSerProGlyGlnIleLeuAspPheTyrThr AlaSerProSerSerCysMetLeuGlnGluLysAlaLeuLysAlaCysPheSerGlyLeu ThrGlnThrGluTrpGlnHisArgHisThrAlaGlnSer.

8. The antibody according to claim 1 which is specific for a peptide fragment of the retinoic acid receptor RAR-β having the amino acid sequence HisGluProLeuThrProSerSerSerGlyAsnThrAlaGluHisSerProSer IleSerProSerSerValGluAsnSerGlyValSerGlnSerProLeuValGln.

9. The antibody according to claim 1 which is polyclonal.

10. The antibody according to claim 1 which is monoclonal.

11. A complex comprising the antibody according to claim 1 bound to a solid support.

* * * * *